(12) United States Patent
Powers et al.

(10) Patent No.: US 7,115,368 B2
(45) Date of Patent: Oct. 3, 2006

(54) DIAGNOSIS AND TREATMENT OF CANCER USING MAMMALIAN PELLINO POLYPEPTIDES AND POLYNUCLEOTIDES

(75) Inventors: Scott Powers, Greenlawn, NY (US); David Mu, Jericho, NY (US); Phil Xiang, San Francisco, CA (US); Yue Peng, South Setauket, NY (US)

(73) Assignee: Amgen SF, LLC, Thousand Oaks, CA (US)

( * ) Notice: Subject to any disclaimer, the term of this patent is extended or adjusted under 35 U.S.C. 154(b) by 508 days.

(21) Appl. No.: 10/041,030

(22) Filed: Dec. 28, 2001

(65) Prior Publication Data

US 2002/0150934 A1    Oct. 17, 2002

Related U.S. Application Data

(60) Provisional application No. 60/259,502, filed on Jan. 2, 2001.

(51) Int. Cl.
*C12Q 1/68* (2006.01)
*C07H 21/02* (2006.01)

(52) U.S. Cl. .............................. 435/6; 435/4; 536/23.1
(58) Field of Classification Search ............... 536/23.1; 435/6, 4
See application file for complete search history.

(56) References Cited

U.S. PATENT DOCUMENTS 4,889,806 A    12/1989    Olson et al.

FOREIGN PATENT DOCUMENTS

| EP | 1 074 617 A2 | 7/2000 |
|---|---|---|
| WO | WO 00/58350 A1 | 10/2000 |
| WO | WO 01/09318 A1 | 2/2001 |
| WO | WO 01/83739 A2 | 11/2001 |
| WO | WO 02/21138 A2 | 3/2002 |

OTHER PUBLICATIONS

Taber's Cyclopedic Medical Dictionary, F.A.Davis and Co, Philadelphia, 1985, p. 274.*
Alberts et al., Molecular Biology of the cell, Garland Publishing, Inc., NY., 1983, pp. 821-822.*
Osband and Ross (Immnology Today, 1990, 11:193-195.*
Bacher, Susanne, et al., "The *Drosophila* proteins Pelle and Tube induce JNK/AP-1 activity in mammalian cells," *FEBS Letters* (2001) 497: 153-158.
Hotta, Kohji, et al., "Characterization of Brachyury-Downstream Notochord Gnees in the *Ciona intestinalis* Embryo," *Development Biology* (2000) 224: 69-80.
Kennedy, E.J. and Moynagh, P.N., "Pellino related intracellular signaling molecule (Pellinol)", (2001) Abstract XP002235786.
Kennedy, E.J. Moynagh, P.N., "PRISM, a novel mediator of Toll/IL-1 signalling,"(2001) Abstract No. XP 002211562.
Resch et al., "Homo sapiens pellino 2(PELI2) mRNA, complete cds," (2000) Abstract XP002235783.
Resch, K. et al., "Assignment of homologous genes, *Peli 1*/PELI1 and *Peli2*/PELI2, for the Pelle adaptor protein Pellino to mouse chromosomes 11 and 14 and human chromosomes 2p13.3 and 14q21, respectively, by physical and radiation hybrid mapping,"*Cytogenetics and Cell Genetics* (2001) 92: 172-174.
Rich, T. et al., "How low can Toll go?" *Trends in Genetics* (2000) 16: 292-294.
Rich, T. et al., "Rellino-related sequences from *Caenorhabditis elegans* and *Homo sapiens,*" *Immunogenetics* (2000) 52:145-149.
Ruben, S.M. et al., "Human colon cancer antigen encoding cDNA SEQ IS No. 787," (2001) Abstract No. XP002235784.
Ruben, S.M. et al. "Human colon cancer antigen encoding cDNA SEQ ID No. 1313," (2001) Abstract No. XP002235785.
Groβhans, J. et al., "Oligomerisation of tube and pelle leads to nuclear localisation of dorsal," Mechanisms of Development, 1999, pp. 127-138, vol. 81.
Sambrook, J., et al., "Expression of Proteins from Cloned Genes," pp. 16.3-16.4, "Introduction of Recombinant Vectors Into Mammalian Cells," P. 16.30, *Molecular Cloning; A Laboratory Manual, Second Edition*, 1989, Cold Spring Harbor Laboratory Press.

* cited by examiner

*Primary Examiner*—Susan Ungar
(74) *Attorney, Agent, or Firm*—Banner & Witcoff, Ltd.

(57) ABSTRACT

The present invention provides methods, reagents, and kits for diagnosing and treating cancer in a mammal, e.g., a human. This invention is based upon the discovery that Pellino 1 or 2 is overexpressed and/or amplified in cancer. Methods to detect cancer or a propensity to develop cancer, to monitor the efficacy of a cancer treatment, and to treat cancer, by inhibiting the expression and/or activity of Pellino 1 or 2 in a cancer cell are included.

4 Claims, 3 Drawing Sheets

FIGURE 1

```
Query:    1 MFSPDQENH--PFKAPVKYGELIVLGYNGSLPNGDRGRRKSRFALFKRPKANGVKPSTVH  58
            MFSP QE H   P K PVKYGEL+VLGYNG+LPNGDRGRRKSRFAL+KRPKANGVKPSTVH
Sbjct:    1 MFSPGQEEHCAPNKEPVKYGELVVLGYNGALPNGDRGRRKSRFALYKRPKANGVKPSTVH  60

Query:   59 IACTPQAAKAISNKDQHSISYTLSRAQTVVVEYTHDSNTDMFQIGRSTESPIDFVVTDTV 118
            +   TPQA+KAIS K QHSISYTLSR QTVVVEYTHD +TDMFQ+GRSTESPIDFVVTDT+
Sbjct:   61 VISTPQASKAISCKGQHSISYTLSRNQTVVVEYTHDKDTDMFQVGRSTESPIDFVVTDTI 120

Query:  119 PGSQSNSDTQSVQSTISRFACRIICERNPPFTARIYAAGFDSSKNIFLGEKAAKWKTSDG 178
                GSQ+  + Q QSTISRFACRI+C+RN P+TARI+AAGFDSSKNIFLGEKAAKWK  DG
Sbjct:  121 SGSQNTDEAQITQSTISRFACRIVCDRNEPYTARIFAAGFDSSKNIFLGEKAAKWKNPDG 180

Query:  179 QMDGLTTNGVLVMHPRNGFTEDSKPGIWREISVCGNVFSLRETRSAQQRGKMVEIETNQL 238
             MDGLTTNGVLVMHPR GFTE+S+PG+WREISVCG+V++LRETRSAQQRGK+VE ETN L
Sbjct:  181 HMDGLTTNGVLVMHPRGGFTEESQPGVWREISVCGDVYTLRETRSAQQRGKLVESETNVL 240

Query:  239 QDGSLIDLCGATLLWRTAEGLSHTPTVKHLEALRQEINAARPQCPVGFNTLAFPSMKRKD 298
            QDGSLIDLCGATLLWRTA+GL HTPT KH+EALRQEINAARPQCPVG NTLAFPS+ RK+
Sbjct:  241 QDGSLIDLCGATLLWRTADGLFHTPTQKHIEALRQEINAARPQCPVGLNTLAFPSINRKE 300

Query:  299 VVDEKQPWVYLNCGHVHGYHNWGNKEERDGKDRECPMCRSVGPYVPLWLGCEAGFYVDAG 358
            VV+EKQPW YL+CGHVHGYHNWG++ +  +  +RECPMCR+VGPYVPLWLGCEAGFYVDAG
Sbjct:  301 VVEEKQPWAYLSCGHVHGYHNWGHRSDTEANERECPMCRTVGPYVPLWLGCEAGFYVDAG 360

Query:  359 PPTHAFSPCGHVCSEKTTAYWSQIPLPHGTHTFHAACPFCAHQLAGEQGYIRLIFQGPLD 418
            PPTHAF+PCGHVCSEK+  YWSQIPLPHGTH FHAACPFCA QL GEQ  I+LIFQGP+D
Sbjct:  361 PPTHAFTPCGHVCSEKSAKYWSQIPLPHGTHAFHAACPFCATQLVGEQNCIKLIFQGPID 420
```

Figure 2

| Tumor cell line | Tumor classification | relative Pellino-2 mRNA |
|---|---|---|
| H460 | large cell | 10673 |
| SKLC-13 | Small cell | 149 |
| LOU-NH91 | squamous | 0.17 |
| H727 | carcinoid | 10748 |
| colo699 | adeno | 1615 |
| EPLC-272H | squamous | 8.2 |
| BEN | Carcinoma | 4652 |
| LCLC-103H | Large cell carcinoma | 12 |
| NCI-H510A | small cell carcinoma | 3074 |
| DMS114 | unknown | 85 |

FIGURE 3

|  |  | Pellino-2 gene copy number | Amp. Frequency |
|---|---|---|---|
| H82 | Lung cell line | 8.9 | 9/43 > 2.5X 21% |
| SKLC-17 | Lung cell line | 3.4 | |
| SKLU-1 | Lung cell line | 2.8 | |
| H322 | Lung cell line | 3.5 | |
| H345 | Lung cell line | 4 | |
| H460 | Lung cell line | 3.3 | |
| SHP77 | Lung cell line | 3.8 | |
| SKLC-13 | Lung cell line | 3.3 | |
| 9812 | Lung cell line | 3.7 | |

|  |  | Pellino-2 gene copy number | Amp. Frequency |
|---|---|---|---|
| LU-2 | lung tumor | 2.6 | 5/43 > 2.5X 12% |
| LU-23 | lung tumor | 2.7 | |
| LU-29 | lung tumor | 2.5 | |
| LU-49 | lung tumor | 3.5 | |
| LU-52 | lung tumor | 3.1 | |

|  |  | Pellino-2 gene copy number | Amp. Frequency |
|---|---|---|---|
| CACO (CC1) | COLON CELL LINE | 2.7 | 7/24 > 2.5X 29% |
| COLO265 (CC2) | COLON CELL LINE | 2.7 | |
| SW48 (CC10) | COLON CELL LINE | 5.5 | |
| COLO300 (CC17) | COLON CELL LINE | 3.1 | |
| colo320 (CC18) | COLON CELL LINE | 3.7 | |
| NULH 716 (CC21) | COLON CELL LINE | 2.5 | |
| SKCO1 (CC23) | COLON CELL LINE | 3.1 | |

|  |  | Pellino-2 gene copy number | Amp. Frequency |
|---|---|---|---|
| CO 1 | colon tumor | 6.9 | 4/30 > 2.5X 13% |
| CO 18 | colon tumor | 2.9 | |
| CO 19 | colon tumor | 2.6 | |
| CO 11 | colon tumor | 3 | |

|  |  | Pellino-2 gene copy number | Amp. Frequency |
|---|---|---|---|
| CHTN273 (OT5) | ovarian tumor | 3 | 5/37 > 2.5X 14% |
| CHTN279 (OT9) | ovarian tumor | 4.2 | |
| CHTN291 (OT18) | ovarian tumor | 3.4 | |
| CHTN380 (OT30) | ovarian tumor | 2.9 | |
| CHTN652 (OT38) | ovarian tumor | 2.6 | |

DIAGNOSIS AND TREATMENT OF CANCER USING MAMMALIAN PELLINO POLYPEPTIDES AND POLYNUCLEOTIDES

CROSS-REFERENCES TO RELATED APPLICATIONS

The current application claims the benefit of U.S. Provisional Application No. 60/259,502, filed Jan. 2, 2001, and now abandoned, which is herein incorporated by reference.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to the field of cancer diagnosis and treatment. Methods and diagnostic reagents are provided for diagnosing and treating cancers that involve amplified Pellino genes and overexpressed Pellino nucleic acids and polypeptides.

BACKGROUND OF THE INVENTION

Cancer is a genetic disease of single cell origin caused by the accumulation of inherited and acquired mutations in specific cancer genes, which have normal cellular functions, but when mutated or present at abnormally high levels contribute to cancer. One type of mutation is gene amplification or overexpression, i.e., where a specific chromosomal region (including the cancer gene) has undergone a relative increase in DNA copy number, such that more copies of the cancer gene are present, or where the level of expression of a gene is increased, such that a correspondingly higher amount of mRNA and protein is produced, causing deleterious effects. Gene amplification is one of the primary genetic alterations in solid tumors, and most of the chromosomal regions that undergo amplification are not well characterized and do not harbor known oncogenes (Knuutila et al., *Am. J. Pathol.* 152:1107–23 (1998); Knuutila et al., *Cancer Genet. Cytogenet.* 100:25–30 (1998)). Discovery of these amplified cancer genes will provide novel targets for diagnostic and therapeutic applications.

The present invention is based on the discovery that Pellino gene, polynucleotide, and polypeptide sequences are amplified and/or overexpressed in cancer cells in mammals. As described herein, this discovery has provided new diagnostic, prognostic, and therapeutic methods for the treatment of cancer, in particular for ovarian and lung cancer.

SUMMARY OF THE INVENTION

The present invention provides methods, reagents, and kits for detecting and treating cancer. In particular, the invention provides Pellino polypeptide and polynucleotide sequences that are amplified and or overexpressed in cancer cells. Accordingly, the present methods can be used to detect cancer or a propensity to develop cancer, to monitor the efficacy of a cancer treatment, to identify inhibitors of Pellino 1 and 2, and to treat cancer, e.g., by inhibiting the expression and/or activity of Pellino 1 and 2 in a cancer cell.

In one aspect, the present invention provides a method of detecting cancer cells in a biological sample from a mammal, the method comprising the steps of providing the biological sample from the mammal, and detecting an overexpression of a Pellino 1 polypeptide comprising at least 70% amino acid identity to SEQ ID NO:2 or a Pellino 2 polypeptide comprising at least 70% amino acid identity to SEQ ID NO:4 in the biological sample, thereby detecting the presence of cancer cells in the biological sample.

In another aspect, the present invention provides a method of detecting cancer cells in a biological sample from a mammal, the method comprising the steps of providing the biological sample from the mammal and detecting an increase in copy number of a gene encoding a Pellino 1 polypeptide comprising at least 70% amino acid identity to SEQ ID NO:2 or a Pellino 2 polypeptide comprising at least 70% amino acid identity to SEQ ID NO:4 in the biological sample, thereby detecting the presence of cancer cells in the biological sample.

In one embodiment, the detecting step comprises contacting the gene with a probe that selectively hybridizes to the gene under conditions in which the probe selectively hybridizes to the gene to form a stable hybridization complex and detecting the hybridization complex. Often, the contacting step includes a step of amplifying the gene in an amplification reaction. In one embodiment, the amplification reaction is a polymerase chain reaction.

In another aspect, the invention provides a method of monitoring the efficacy of a therapeutic treatment of cancer, the method comprising the steps of providing a biological sample from a mammal undergoing the therapeutic treatment, and detecting a level of a Pellino 1 polypeptide comprising at least 70% amino acid identity to SEQ ID NO:2 or a Pellino 2 polypeptide comprising at least 70% amino acid identity to SEQ ID NO:4 in the biological sample compared to a level in a biological sample from the mammal prior to, or earlier in, the therapeutic treatment, thereby monitoring the efficacy of the therapy.

In one embodiment, the Pellino 1 polypeptide has an amino acid sequence of SEQ ID NO:2 or the Pellino 2 polypeptide has an amino acid sequence of SEQ ID NO:4.

In one embodiment overexpression is at least 1.5-fold. Alternatively, overexpression is 5-fold or above.

The method includes an embodiment in which the Pellino polypeptide is detected using an antibody that selectively binds to Pellino 1 and/or 2. Often, the amount of Pellino polypeptide is quantified by immunoassay. In another embodiment, detecting the overexpression of a Pellino polypeptide comprises detecting the activity of the Pellino polypeptide.

In an alternative embodiment, detecting overexpression of a Pellino polypeptide comprises detecting an mRNA that encodes the Pellino polypeptide. Often the mRNA is detected using an amplification reaction.

In one embodiment, the cancer cells are from an epithelial cell. In one embodiment, the cancer cell is an ovarian, colon, or lung cancer. In other embodiments, the mammal is a human and the biological sample is a tissue biopsy, often from ovarian. colon, or lung tissue.

The invention also provides a method of identifying a compound that inhibits the activity of a Pellino polypeptide, the method comprising the steps of contacting the compound with a Pellino 1 polypeptide comprising at least 70% amino acid identity to SEQ ID NO:2 or a Pellino 2 polypeptide comprising at least 70% amino acid identity to SEQ ID NO:4 and detecting a decrease in the activity of the Pellino 1 or 2 polypeptide.

In one embodiment, the polypeptide is linked to a solid phase. In another embodiment, the Pellino polypeptide is expressed in a cell. Additionally, the Pellino polypeptide can be amplified in the cell compared to normal.

In another aspect, the invention provides a method of treating a cancer or inhibiting proliferation of a cancer cell that overexpresses a Pellino 1 polypeptide comprising at least 70% amino acid identity to SEQ ID NO:2 or a Pellino 2 polypeptide comprising at least 70% amino acid identity to SEQ ID NO:4, the method comprising the step of contacting the cancer cell with a therapeutically effective amount of an inhibitor of the Pellino 1 or 2 polypeptide.

In one embodiment, the inhibitor is an antibody. Alternatively, the inhibitor is an antisense polynucleotide.

In one aspect, the present invention provides an isolated nucleic acid encoding a Pellino 2 polypeptide, wherein the Pellino 2 polypeptide comprises at least 95% amino acid sequence identity to SEQ ID NO:4.

In one embodiment, the nucleic acid encodes a Pellino 2 polypeptide comprising an amino acid sequence of SEQ ID NO:4. In one embodiment, the nucleic acid comprises a nucleotide sequence of SEQ ID NO:3.

In another aspect, the present invention provides an expression vector and a host cell comprising an isolated nucleic acid encoding a Pellino 2 polypeptide, wherein the Pellino 2 polypeptide comprises at least 95% amino acid sequence identity to SEQ ID NO:4.

In another aspect, the present invention provides an isolated Pellino 2 polypeptide comprising at least 95% amino acid identity to SEQ ID NO:4.

In one embodiment, the polypeptide comprises an amino acid sequence of SEQ ID NO:4. In one embodiment, the polypeptide specifically binds to antibodies generated against a polypeptide comprising an amino acid sequence of SEQ ID NO:4.

In another aspect, the present invention provides an antibody that binds to a Pellino 2 polypeptide that comprises at least 95% amino acid sequence identity to SEQ ID NO:4.

BRIEF DESCRIPTION OF THE DRAWINGS

FIG. 1 shows a comparison of Pellino 1 (SEQ ID NO:2) and Pellino 2 (SEQ ID NO:4) amino acids sequences. The two sequences exhibit approximately 81% amino acid identity (amino acid sequence identity=SEQ ID NOS:13–42).

FIG. 2 shows Pellino 2 mRNA overexpression in tumor cell lines.

FIG. 3 shows amplification of the Pellino 2 gene in cancer cells.

DETAILED DESCRIPTION OF THE INVENTION

Introduction

The present invention provides methods, reagents, and kits for diagnosing and treating cancer. The invention is based upon the discovery that Pellino 1 and Pellino 2 genes are overexpressed and amplified in cancer cells, particularly lung and ovarian cancer cells. Accordingly, the present methods can be used to detect cancer or a propensity to develop cancer, to monitor the efficacy of a cancer treatment, and to treat cancer, e.g., by inhibiting the expression and/or activity of Pellino 1 or Pellino 2 in a cancer cell.

*Drosophila* Pellino was originally identified as a protein that associates with the kinase domain of activated Pelle, thereby participating in intracellular transduction of an extracellular signal, leading to nuclear localization of Dorsal, a member of the Rel family expressed in *Drosophila* embryos, and a member of the Dorsal/Cactus complex (see, e.g., Grosshans et al., *Mech. Dev.* 81:127–138 (1999)). *Drosophila* Pellino therefore serves as an adaptor to link kinase signaling to downstream effectors. Pellino genes and gene products include human Pellino 1 mRNA (SEQ ID NO:1), Accession No. AF302505.1 (complete cds) and AJ278859.1 (ORF 1); human Pellino 1 protein (SEQ ID NO:2) (LOC57334), mRNA NM_020651.1; mouse Pellino 1 mRNA, Accession No. AF302503.1 (complete cds); human Pellino 2 mRNA, Accession No. AF302502.1 (complete cds); mouse Pellino 2 mRNA, Accession No. AF302504.1 (complete cds); *Drosophila melanogaster* Pellino mRNA, Accession No. AF091624.1; *Caenorhabditis elegans* Pellino mRNA, Accession No. AJ288951.1; and *Ciona intestinalis* Pellino mRNA, Accession No. AB036851.1.

The methods of the invention typically involve detecting the presence of Pellino 1 or 2 in a biological sample taken from a mammal. In certain embodiments, a level of Pellino 1 or 2 in a biological sample will be compared with a control sample taken from a cancer-free animal, or, preferably, with a value expected for a sample taken from a cancer-free animal. A control sample can also be obtained from normal tissue from the same mammal that is suspected to have cancer.

The ability to detect cancer cells by virtue of an increased level of Pellino 1 or 2 is useful for any of a large number of applications. For example, an increased level of Pellino 1 or 2 in cells of a mammal can be used, alone or in combination with other diagnostic methods, to diagnose cancer in the mammal or to determine the propensity of a mammal to develop cancer over time. The detection of Pellino 1 or 2 can also be used to monitor the efficacy of a cancer treatment and to provide a prognosis, e.g., for overall and disease free survival. For example, a level of a Pellino 1 or 2 polypeptide or polynucleotide after an anti-cancer treatment is compared to the level in the mammal before the treatment. A decrease in the level of the Pellino 1 or 2 polypeptide or polynucleotide after the treatment indicates efficacious treatment.

An increased level or diagnostic presence of Pellino 1 or 2 can also be used to influence the choice of anti-cancer treatment in a mammal and provide a prognosis for outcome with a certain treatment, where, for example, the level of Pellino 1 or 2 increase directly correlates with the aggressiveness of the anti-cancer therapy. For example, an increased level of Pellino 1 or 2 in tumor cells can indicate that the use of an agent that decreases proliferation would be effective in treating the tumor.

In addition, the ability to detect cancer cells can be useful to monitor the number or location of cancer cells in a patient, in vivo or in vitro, for example, to monitor the progression of the cancer over time. In addition, the level or presence or absence of Pellino 1 or 2 can be statistically correlated with the efficacy of particular anti-cancer therapies or with observed prognostic outcomes, thereby allowing the development of databases based on which a statistically-based prognosis, or a selection of the most efficacious treatment, can be made in view of a particular level or diagnostic presence of Pellino 1 or 2.

The present invention also provides methods for treating cancer. In certain embodiments, the proliferation of a cell with an elevated level of Pellino 1 or 2 polynucleotides, polypeptides, or polypeptide activity is inhibited. The proliferation is decreased by, for example, contacting the cell with an inhibitor of Pellino 1 or 2 transcription or translation, or an inhibitor of the activity of a Pellino 1 or 2 polypeptide. Such inhibitors include, but are not limited to, antisense polynucleotides, ribozymes, antibodies, dominant negative Pellino 1 or 2 polypeptides, and small molecule inhibitors of Pellino 1 or 2 activity.

The present methods can be used to diagnose, determine the prognosis for, or treat, any of a number of types of cancers. In preferred embodiments, the cancer is an epithelial cancer, e.g., colorectal, lung, breast, prostate, kidney, stomach, bladder, or ovarian cancer, or any cancer of the gastrointestinal tract. In a particularly preferred embodiment, the cancer is lung, colon, or ovarian cancer.

The diagnostic methods of this invention can be used in animals including, for example, primates, canines, felines, murines, bovines, equines, ovines, porcines, lagomorphs, etc, as well as in humans.

Kits are also provided for carrying out the herein-disclosed diagnostic and therapeutic methods.

Definitions

The phrase "detecting a cancer" or "diagnosing a cancer" refers to determining the presence or absence of cancer or a precancerous condition in an animal. "Detecting a cancer" can also refer to obtaining indirect evidence regarding the likelihood of the presence of cancerous cells in the animal. Detecting a cancer can be accomplished using the methods of this invention alone, in combination with other methods, or in light of other information regarding the state of health of the animal.

A "cancer" in an animal refers to the presence of cells possessing characteristics typical of cancer-causing cells, such as uncontrolled proliferation, immortality, metastatic potential, rapid growth and proliferation rate, and certain characteristic morphological features and cellular markers. In some circumstances, cancer cells will be in the form of a tumor, but such cells may exist alone within an animal, or may circulate in the blood stream as independent cells, such as leukemic cells.

The term "Pellino" therefore refers to Pellino 1 and Pellino 2 nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 50, 100, 200, 500, 1000, or more amino acids, to a Pellino sequence of SEQ ID NO:2 or a Pellino 2 sequence of SEQ ID NO:4; (2) bind to antibodies, e.g., polyclonal antibodies, raised against an immunogen comprising an amino acid sequence of SEQ ID NO:2 or SEQ ID NO:4, and conservatively modified variants thereof; (3) specifically hybridize under stringent hybridization conditions to a Pellino 1 or 2 nucleic acid sequence of SEQ ID NO:1 or SEQ ID NO:3 and conservatively modified variants thereof; (4) have a nucleic acid sequence that has greater than about 95%, preferably greater than about 96%, 97%, 98%, 99%, or higher nucleotide sequence identity, preferably over a region of at least about 50, 100, 200, 500, 1000, or more nucleotides, to SEQ ID NO:1 or SEQ ID NO:3; or (5) for Pellino 2, are amplified by primers that specifically hybridize under stringent hybridization conditions to the same sequence as a primer set selected from the group consisting of ATGTTTTCCCCTG-GCCAGGAGGAACAC (PELD1) (SEQ ID NO:5) and TCAGTCAATTGGACCTTGGAAAATTAA (PELD2) (SEQ ID NO:6). A Pellino polynucleotide or polypeptide sequence is typically from a mammal including, but not limited to, human, rat, mouse, hamster, cow, pig, horse, sheep, or any mammal. A "Pellino polynucleotide" and a "Pellino polypeptide," are both either naturally occurring or recombinant. The human Pellino 2 gene is located at chromosome 14Q21. As described above, Pellino polypeptides bind to the Pelle kinase and participate in signal transduction (see, e.g., GroBhans et al, Mechanisms of Development 81:127–138 (1999)).

The "level of Pellino mRNA" in a biological sample refers to the amount of mRNA transcribed from a Pellino gene that is present in a cell or a biological sample. The mRNA generally encodes a Pellino protein, often fully functional, although mutations or microdeletions may be present that alter or eliminate the function of the encoded protein. A "level of Pellino mRNA" need not be quantified, but can simply be detected, e.g., a subjective, visual detection by a human, with or without comparison to a level from a control sample or a level expected of a control sample.

The "level of Pellino protein or polypeptide" in a biological sample refers to the amount of polypeptide translated from a Pellino mRNA that is present in a cell or biological sample. The polypeptide may or may not have Pellino protein activity. A "level of Pellino protein" need not be quantified, but can simply be detected, e.g., a subjective, visual detection by a human, with or without comparison to a level from a control sample or a level expected of a control sample.

A "full length" Pellino protein or nucleic acid refers to a Pellino polypeptide or polynucleotide sequence, or a variant thereof, that contains all of the elements normally contained in one or more naturally occurring, wild type Pellino polynucleotide or polypeptide sequences.

"Biological sample" as used herein is a sample of biological tissue or fluid that contains nucleic acids or polypeptides of Pellino 1 and 2. Such samples include, but are not limited to, tissue isolated from humans, mice, and rats,. Biological samples may also include sections of tissues such as frozen sections taken for histologic purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as chimpanzees or humans.

"Providing a biological sample" means to obtain a biological sample for use in the methods described in this invention. Most often, this will be done by removing a sample of cells from an animal, but can also be accomplished by using previously isolated cells (e.g., isolated by another person, at another time, and/or for another purpose), or by performing the methods of the invention in vivo.

A "control sample" refers to a sample of biological material representative of healthy, cancer-free animals. The level of Pellino 1 or 2 in a control sample is desirably typical of the general population of normal, cancer-free animals. This sample can be removed from an animal expressly for use in the methods described in this invention, or can be any biological material representative of normal, cancer-free animals. A control sample can also be obtained from normal tissue from the animal that has cancer or is suspected of having cancer. A control sample can also refer to an established level of Pellino 1 or 2, representative of the cancer-free population, that has been previously established based on measurements from normal, cancer-free animals. If a detection method is used that only detects Pellino 1 or 2 when a level higher than that typical of a normal, cancer-free animal is present, i.e., an immunohistochemical assay giving a simple positive or negative result, this is considered to be assessing the Pellino 1 or 2 level in comparison to the control level, as the control level is inherent in the assay.

"Overexpression" or an "increased," or "elevated," level of a Pellino polynucleotide or protein refers to a level of Pellino 1 or 2 polynucleotide or polypeptide, that, in comparison with a control level of Pellino 1 or 2, is detectably higher. The method of comparison can be statistical, using quantified values for the level of Pellino, or can be compared using nonstatistical means, such as by a visual, subjective assessment by a human.

A level of Pellino polypeptide or polynucleotide that is "expected" in a control sample refers to a level that represents a typical, cancer-free sample, and from which an elevated, or diagnostic, presence of Pellino polypeptide or polynucleotide can be distinguished. Preferably, an "expected" level will be controlled for such factors as the age, sex, medical history, etc. of the mammal, as well as for the particular biological sample being tested.

The phrase "functional effects" in the context of assays for testing compounds that modulate Pellino activity includes the determination of any parameter that is indirectly or directly under the influence of Pellino, e.g., a functional, physical, or chemical effect, such as the ability to bind to activated Pelle kinase. It includes binding activity, signal transduction, the ability of cells to proliferate, gene amplification, or expression in cancer cells, and other characteristics of transformed cells. "Functional effects" include in vitro, in vivo, and ex vivo activities.

By "determining the functional effect" is meant assaying for a compound that increases or decreases a parameter that is indirectly or directly under the influence of Pellino 1 or 2, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties for the protein, measuring inducible markers or transcriptional activation of Pellino 1 or 2; measuring binding activity or binding assays, e.g., ATP binding, and measuring cellular proliferation; measuring signal transduction; measuring cellular transformation, etc.

"Inhibitors" and "modulators" of Pellino 1 and 2 are used to refer to inhibitory or modulating molecules identified using in vitro and in vivo assays of Pellino 1 and 2. Inhibitors are compounds that, e.g. bind to, partially or totally block activity, decrease, prevent, delay activation, inactivate, desensitize, or down regulate the activity of Pellino 1 and 2, e.g., antagonists. Inhibitors or modulators also include genetically modified versions of Pellino 1 and 2, e.g., versions with altered activity, as well as naturally occurring and synthetic ligands, antagonists, agonists, antibodies, small chemical molecules and the like. Such assays for inhibitors and activators include, e.g., expressing Pellino 1 and 2 in vitro, in cells, or cell membranes, applying putative modulator compounds, and then determining the functional effects on Pellino activity, as described above.

Samples or assays comprising Pellino 1 and/or 2 that are treated with a potential activator, inhibitor, or modulator are compared to control samples without the inhibitor, activator, or modulator to examine the extent of inhibition. Control samples (untreated with inhibitors) are assigned a relative Pellino activity value of 100%. Inhibition of a Pellino polypeptide is achieved when the Pellino activity value relative to the control is about 80%, preferably 50%, more preferably 25–0%. Activation of a Pellino polypeptide is achieved when the Pellino activity value relative to the control (untreated with activators) is 110%, more preferably 150%, more preferably 200–500% (i.e., two to five fold higher relative to the control), more preferably 1000–3000% higher.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated Pellino nucleic acid is separated from open reading frames that flank a Pellino gene and encode proteins other than Pellino 1 or 2. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiralmethyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells such as CHO, HeLa, and the like.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I:* *The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins for which ant or 7 can be made detectable, e.g., by incorporating a radiolabel into the peptide, and used to detect antibodies specifically reactive with the peptide).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., SEQ ID NOS:1–4), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to the compliment of a test sequence. The definition also includes sequences that have deletions and/or additions, as well as those that have substitutions. As described below, the preferred algorithms can account for gaps and the like. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM 62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec–2 min., an annealing phase lasting 30 sec.–2 min., and an extension phase of about 72° C. for 1–2 min.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$–$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990))

For preparation of antibodies, e.g., recombinant, monoclonal, or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-Pellino" antibody is an antibody or antibody fragment that specifically binds a polypeptide encoded by a Pellino gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, antibodies raised to a particular Pellino polypeptide can be selected to obtain only those antibodies that are specifically immunoreactive with the Pellino polypeptide, e.g., Pellino 1 or 2, and not with other proteins, except for polymorphic variants, orthologs, and alleles of the specific Pellino polypeptide. In addition, antibodies raised to a particular Pellino polypeptide ortholog can be selected to obtain only those antibodies that are specifically immunoreactive with the Pellino polypeptide ortholog, e.g., human Pellino 1 or 2, and not with other orthologous proteins, except for polymorphic variants, mutants, and alleles of the Pellino polypeptide ortholog. This selection may be achieved by subtracting out antibodies that cross-react with desired Pellino molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

Detecting Pellino Polynucleotides and Polypeptides

Detection of Pellino 1 and Pellino 2 polynucleotides and polypeptides can involve quantitative or qualitative detection of the polypeptide or polynucleotide, and can involve an actual comparison with a control value or, alternatively, may be performed so that the detection itself inherently indicates an increased level, or "diagnostic presence" of Pellino 1 or Pellino 2. As used herein, a "diagnostic presence" indicates any level of Pellino 1 or Pellino 2 that is greater than that expected in a noncancerous sample. In a one embodiment, assays for a Pellino 1 or Pellino 2 polypeptide or polynucleotide in a biological sample are conducted under conditions wherein a normal level of Pellino polypeptide or polynucleotide, i.e., a level typical of a noncancerous sample, i.e., cancer-free, would not be detected. In such assays, therefore, the detection of any Pellino polypeptide or nucleic acid in the biological sample indicates a diagnostic presence, or increased level.

In certain embodiments, the level of Pellino 1 or Pellino 2 polynucleotide, polypeptide, or protein activity will be quantified. In such embodiments, the difference between an elevated level of Pellino 1 or Pellino 2 and a normal, control level will preferably be statistically significant. Typically, a diagnostic presence, i.e., overexpression or an increase of Pellino 1 or Pellino 2 polypeptide or nucleic acid, represents at least about a 1.5, 2, 5, 10, or greater fold increase in the level of Pellino 1 or Pellino 2 polypeptide or polynucleotide in the biological sample compared to a level expected in a noncancerous sample. Detection of Pellino 1 or Pellino 2 can be performed in vitro, i.e., in cells within a biological sample taken from the mammal, or in vivo.

As described below, any of a number of methods to detect Pellino 1 or Pellino 2 can be used. A Pellino 1 or Pellino 2 polynucleotide level can be detected by detecting any Pellino 1 or Pellino 2 or RNA, including Pellino 1 or Pellino 2 genomic DNA, mRNA, and cDNA. A Pellino 1 or Pellino 2 polypeptide can be detected by detecting a Pellino 1 or Pellino 2 polypeptide itself, or by detecting Pellino 1 or Pellino 2 protein activity. Detection can involve quantification of the level of Pellino 1 or Pellino 2 (e.g., genomic DNA, cDNA, mRNA, or protein level, or protein activity), or, alternatively, can be a qualitative assessment of the level, or of the presence or absence, of Pellino 1 or Pellino 2, in particular in comparison with a control level. Any of a number of methods to detect any of the above can be used, as described infra. Such methods include, for example, hybridization, amplification, and other assays.

In certain embodiments, the ability to detect an increased level, or diagnostic presence, in a cell is used as a marker for cancer cells, i.e., to monitor the number or localization of cancer cells in a patient, as detected in vivo or in vitro.

Typically, the Pellino 1 or Pellino 2 polynucleotides or polypeptides detected herein will be at least about 70% identical, and preferably 75%, 80%, 85%, 90%, 91%, 92%, 93%, 94%, 95%, 96%, 97%, 98%, 99% or more identical, over a region of at least about 50, 100, 200, or more nucleotides, or 20, 50, 100, or more amino acids, to SEQ ID NO:1–4, or to one or more Pellino 1 or Pellino 2 sequences available, e.g., from GenBank (see, e.g., human Pellino 1 mRNA, Accession No. AF302505.1 (complete cds) and AJ278859.1 (ORF 1); human Pellino 1 protein (LOC57334), mRNA NM_020651.1; mouse Pellino 1 mRNA, Accession No. AF302503.1 (complete cds); human Pellino 2 mRNA, Accession No. AF302502.1 (complete cds); mouse Pellino 2 mRNA, Accession No. AF302504.1 (complete cds); *Drosophila melanogaster* Pellino mRNA, Accession No. AF091624.1; *Caenorhabditis elegans* Pellino mRNA, Accession No. AJ288951.1; and *Ciona intestinalis* Pellino mRNA, Accession No. AB036851.1.). Such polynucleotides or polypeptides can represent functional or nonfunctional forms of Pellino 1 or 2, or any variant, derivative, or fragment thereof.

Typically, the level and/or presence of Pellino 1 or 2 polynucleotides or polypeptides will be detected in a biological sample. A "biological sample" refers to a cell or population of cells or a quantity of tissue or fluid from an animal. Most often, the sample has been removed from an animal, but the term "biological sample" can also refer to cells or tissue analyzed in vivo, i.e., without removal from the animal. Typically, a "biological sample" will contain cells from the animal, but the term can also refer to noncellular biological material, such as noncellular fractions of blood, saliva, or urine, that can be used to measure Pellino 1 or 2 levels. Numerous types of biological samples can be used in the present invention, including, but not limited to, a tissue biopsy, a blood sample, a buccal scrape, a saliva sample, or a nipple discharge.

As used herein, a "tissue biopsy" refers to an amount of tissue removed from an animal for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc.

Detection of Copy Number

In one embodiment, the presence of cancer is evaluated by determining the copy number of Pellino 1 or 2 genes, i.e., the number of DNA sequences in a cell encoding a Pellino 1 or 2 protein. Generally, for a given autosomal gene, an animal has two copies of each gene. The copy number can be increased, however, by gene amplification or duplication, e.g., in cancer cells, or reduced by deletion. Methods of evaluating the copy number of a particular gene are well known to those of skill in the art, and include, inter alia, hybridization and amplification based assays.

Hybridization-based Assays

Any of a number of hybridization based assays can be used to detect the copy number of Pellino 1 or 2 genes in the cells of a biological sample. One such method is by Southern blot. In a Southern blot, genomic DNA is typically fragmented, separated electrophoretically, transferred to a membrane, and subsequently hybridized to a Pellino 1 or 2 specific probe. Comparison of the intensity of the hybridization signal from the probe for the target region with a signal from a control probe for a region of normal genomic DNA (e.g., a nonamplified portion of the same or related cell, tissue, organ, etc.) provides an estimate of the relative Pellino 1 or 2 copy number. Southern blot methodology is well known in the art and is described, e.g., in Ausubel et al., or Sambrook et al., supra.

An alternative means for determining the copy number of Pellino 1 or 2 genes in a sample is by in situ hybridization, e.g., fluorescence in situ hybridization, or FISH. In situ hybridization assays are well known (e.g., Angerer (1987) Meth. Enzymol 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments.

The probes used in such applications are typically labeled, e.g., with radioisotopes or fluorescent reporters. Preferred probes are sufficiently long, e.g., from about 50, 100, or 200 nucleotides to about 1000 or more nucleotides, so as to specifically hybridize with the target nucleic acid(s) under stringent conditions.

In numerous embodiments, "comparative probe" methods, such as comparative genomic hybridization (CGH), are used to detect Pellino 1 or 2 gene amplification. In comparative genomic hybridization methods, a "test" collection of nucleic acids is labeled with a first label, while a second collection (e.g., from a healthy cell or tissue) is labeled with a second label. The ratio of hybridization of the nucleic acids is determined by the ratio of the first and second labels binding to each fiber in an array. Differences in the ratio of the signals from the two labels, e.g., due to gene amplification in the test collection, is detected and the ratio provides a measure of the Pellino 1 or 2 gene copy number.

Hybridization protocols suitable for use with the methods of the invention are described, e.g., in Albertson (1984) *EMBO J.* 3: 1227–1234; Pinkel (1988) *Proc. Natl. Acad. Sci. USA* 85: 9138–9142; EPO Pub. No. 430,402; *Methods in Molecular Biology, Vol. 33: In Situ Hybridization Protocols*, Choo, ed., Humana Press, Totowa, N.J. (1994), etc.

Amplification-Based Assays

In another embodiment, amplification-based assays are used to measure the copy number of Pellino 1 or 2 genes. In such assays, the Pellino 1 or 2 nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the copy number of the Pellino 1 or 2 gene. Methods of quantitative amplification are well known to those of skill in the art. Detailed protocols for quantitative PCR are provided, e.g., in Innis et al. (1990) *PCR Protocols, A Guide to Methods and Applications*, Academic Press, Inc. N.Y.). The known nucleic acid sequence for Pellino 1 or 2 (see, e.g., SEQ ID NO:1 or 3) is sufficient to enable one of skill to routinely select primers to amplify any portion of the gene.

In preferred embodiments, a TAQMAN® based assay is used to quantify Pellino 1 or 2 polynucleotides. TAQMAN® based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AMPLITAQ®, results in the cleavage of the TAQMAN® probe. This cleavage separates the 5' fluorescent dye and the 3' quenching agent, thereby resulting in an increase in fluorescence as a function of amplification (see, for example, literature provided by Perkin-Elmer).

Other suitable amplification methods include, but are not limited to, ligase chain reaction (LCR) (see, Wu and Wallace (1989) *Genomics* 4: 560, Landegren et al. (1988) *Science* 241: 1077, and Barringer et al. (1990) *Gene* 89: 117), transcription amplification (Kwoh et al. (1989) *Proc. Natl Acad. Sci. USA* 86: 1173), self-sustained sequence replication (Guatelli et al. (1990) *Proc. Nat. Acad. Sci. USA* 87: 1874), dot PCR, and linker adapter PCR, etc.

Detection of Pellino 1 or 2 mRNA Expression

Direct Hybridization-based Assays

Methods of detecting and/or quantifying the level of Pellino 1 or 2 gene transcripts (mRNA or cDNA made therefrom) using nucleic acid hybridization techniques are known to those of skill in the art (see, Sambrook et al., (1989) *Molecular Cloning: A Laboratory Manual,* 2d Ed., vols 1–3, Cold Spring Harbor Press, New York).

For example, one method for evaluating the presence, absence, or quantity of Pellino 1 or 2 cDNA involves a Northern blot. In brief, in a typical embodiment, mRNA is isolated from a given biological sample, electrophoresed to separate the mRNA species, and transferred from the gel to a nitrocellulose membrane. Labeled Pellino 1 or 2 probes are then hybridized to the membrane to identify and/or quantify the mRNA.

Amplification-based Assays

In another embodiment, a Pellino 1 or 2 transcript (e.g., Pellino 1 or 2 mRNA) is detected using amplification-based methods (e.g., RT-PCR). RT-PCR methods are well known to those of skill (see, e.g., Ausubel et al., supra). Preferably, quantitative RT-PCR is used, thereby allowing the comparison of the level of mRNA in a sample with a control sample or value.

Detection of Pellino 1 or 2 Polypeptide Expression

In addition to the detection of Pellino 1 or 2 genes and gene expression using nucleic acid hybridization technology, Pellino 1 or 2 levels can also be detected and/or quantified by detecting or quantifying the polypeptide. Pellino 1 or 2 polypeptide can be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In a preferred embodiment, a Pellino 1 or 2 polypeptide is detected using an immunoassay such as an ELISA assay (see, e.g., Crowther, John R. *ELISA Theory and Practice.* Humana Press: New Jersey, 1995). As used herein, an "immunoassay" is an assay that utilizes an antibody to specifically bind to Pellino 1 or 2.

Antibodies to Pellino 1 and 2

Methods of producing polyclonal and monoclonal antibodies that react specifically with Pellino 1 or 2 polypeptides are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)). Such antibodies can be used for therapeutic and diagnostic applications, e.g., in the treatment and/or detection of colon cancer.

A number of Pellino 1 or 2 peptides or a full length protein may be used to produce antibodies specifically reactive with Pellino 1 or 2 protein. For example, a recombinant Pellino 1 or 2 or an antigenic fragment thereof, is isolated as described herein. For example, recombinant Pellino 1 or 2 protein can be expressed in eukaryotic or prokaryotic cells and purified using standard methods. Recombinant protein is the preferred immunogen for the production of monoclonal or polyclonal antibodies. Alternatively, a synthetic peptide derived from any Pellino 1 or 2 amino acid sequence can be conjugated to a carrier protein and used as an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the Pellino 1 or 2 protein. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non- Pellino 1 or 2 proteins or even other related proteins from other organisms, using a competitive binding immunoassay. Specific polyclonal antisera and monoclonal antibodies will usually bind with a $K^d$ of at least about 0.1 mM, more usually at least about 1 µM, preferably at least about 0.1 µM or better, and most preferably, 0.01 µM or better.

Once specific antibodies to Pellino 1 or 2 are available, Pellino 1 or 2 proteins can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

Immunological Binding Assays

Pellino 1 or 2 polypeptides can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology:*

*Antibodies in Cell Biology*, volume 37 (Asai, ed. 1993); *Basic and Clinical Immunology* (Stites & Terr, eds., 7th ed. 1991).

Immunoassays typically use direct or indirect labeling agents to label the complex formed by the antibody and antigen. The labeling agent can itself be one of the moieties comprising the antibody/antigen complex, i.e., a direct labeling agent. Thus, the labeling agent may be a labeled Pellino 1 or 2 polypeptide or a labeled anti- Pellino 1 or 2 antibody. Alternatively, the labeling agent can be a third moiety, such as a secondary antibody, that specifically binds to the antibody/ Pellino 1 or 2 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non competitive assay formats: Immunoassays for detecting Pellino 1 or 2 in samples can be either competitive or noncompetitive. Noncompetitive immunoassays are assays in which the amount of antigen is directly measured. In one preferred "sandwich" assay, for example, the anti- Pellino 1 or 2 antibodies can be bound directly to a solid substrate on which they are immobilized. These immobilized antibodies then capture Pellino 1 or 2 proteins present in the test sample. The Pellino 1 or 2 protein thus immobilized is then bound by a labeling agent, such as a second Pellino 1 or 2 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive assay formats: In competitive assays, the amount of Pellino 1 or 2 protein present in a sample is measured indirectly, e.g., by measuring the amount of added (exogenous) Pellino 1 or 2 displaced (or competed away) from an anti- Pellino 1 or 2 antibody by Pellino 1 or 2 protein present in a sample. For example, a known amount of labeled Pellino 1 or 2 polypeptide is added to a sample and the sample is then contacted with an anti- Pellino 1 or 2 antibody. The amount of labeled Pellino 1 or 2 polypeptide bound to the antibody is inversely proportional to the concentration of Pellino 1 or 2 polypeptide present in the sample. In one embodiment, the antibody is immobilized on a solid substrate. The amount of Pellino 1 or 2 bound to the antibody may be determined either by measuring the amount of Pellino 1 or 2 present in a Pellino 1 or 2/antibody complex, or alternatively by measuring the amount of remaining uncomplexed protein. The amount of Pellino 1 or 2 may be detected by providing a labeled Pellino 1 or 2 molecule.

A hapten inhibition assay is another competitive assay. In this assay the known Pellino 1 or 2 is immobilized on a solid substrate. A known amount of anti-Pellino 1 or 2 antibody is added to the sample, and the sample is then contacted with the immobilized Pellino 1 or 2. The amount of anti- Pellino 1 or 2 antibody bound to the known immobilize Pellino 1 or 2 is inversely proportional to the amount of Pellino 1 or 2 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Other assay formats: Western blot (immunoblot) analysis can also be used to detect and quantify the presence of Pellino 1 or 2 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind Pellino 1 or 2. The anti- Pellino 1 or 2 antibodies specifically bind to the Pellino 1 or 2 on the solid support. These antibodies can be directly labeled or indirectly detected using labeled antibodies (e.g., labeled sheep anti-mouse antibodies) that specifically bind to the anti- Pellino 1 or 2 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of non-specific binding: One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels: The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label can be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions. For a review of various labeling or signal producing systems that maybe used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Detection of Pellino Protein Activity

In another embodiment, Pellino 1 and 2 polypeptide levels are determined by assaying Pellino 1 and 2 protein activity in a biological sample. Such protein activity can be measured using standard techniques known in the art and can be directly or indirectly measured. Measures of Pellino activity typically includes assessment of the binding of Pellino 1 or 2 to a kinase (e.g., radioactive ligand binding) and downstream effects on signal transduction, e.g., second messenger levels(e.g., cAMP, cGMP, $IP_3$, DAG, or $Ca^{2+}$), ion flux, phosphorylation levels, transcription levels, and the like. For a general review of methods of assaying signal transduction, see, e.g., Methods in Enzymology, vols. 237 and 238 (1994) and volume 96 (1983); Bourne et al., Nature 10:349:117–27 (1991); Bourne et al., Nature 348:125–32 (1990); Pitcher et al., Annu. Rev. Biochem. 67:653–92 (1998).

Pellino 1 and 2 activity can be measured using a variety of assays known in the art. In one embodiment, substrates for kinases can be measured by the transfer of $^{32}P$ from gamma-labeled ATP or GTP to the substrate, which can be assayed with a scintillation counter. In another embodiment, ligand binding of Pellino, or a Pellino binding domain or chimeric protein containing the binding domain, to its substrate can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

Extracellular events initiate subsequent intracellular events, e.g., increases in second messengers such as IP3, which releases intracellular stores of calcium ions. Activation of some pathways stimulates the formation of inositol triphosphate (IP3) through phospholipase C-mediated hydrolysis of phosphatidylinositol (Berridge & Irvine, Nature 312:315–21 (1984)). IP3 in turn stimulates the release of intracellular calcium ion stores. Thus, a change in cytoplasmic calcium ion levels, or a change in second messenger levels such as IP3 can be used to assess the activity of the Pellino signal transduction cascade. In some cases it may be desirable although not necessary to conduct such assays in calcium-free buffer, optionally supplemented with a chelating agent such as EGTA, to distinguish fluorescence response resulting from calcium release from internal stores.

In one embodiment, changes in intracellular cAMP or cGMP can be measured using immunoassays. The method described in Offermanns & Simon, J. Biol. Chem. 270: 15175–15180 (1995) may be used to determine the level of cAMP. Also, the method described in Felley-Bosco et al., Am. J. Resp. Cell and Mol. Biol. 11:159–164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with $^3H$-myoinositol for 48 or more hrs. The labeled cells are treated with a test compound for one hour. The treated cells are lysed and extracted in chloroform-methanol-water after which the inositol phosphates are separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on signal transduction. A host cell containing the protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, Nature Biotechnology 15:961–964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

Diagnosing Cancer

The present methods can be used to diagnose and treat any of a number of types of cancers. In preferred embodiments, cancers such as epithelial-derived cancers will be diagnosed and/or treated, e.g., lung, colon, and ovarian cancer. Other epithelial cancers include, e.g., breast, kidney, stomach, bladder, and colorectal cancers. A cancer at any stage of progression can be detected, such as primary, metastatic, and recurrent cancers. Information regarding numerous types of cancer can be found, e.g., from the American Cancer Society, or from, e.g., Wilson et al. (1991) Harrison's Principles of Internal Medicine, $12^{th}$ Edition, McGraw-Hill, Inc.

The present invention provides numerous methods for determining whether or not a mammal has cancer, whether or not a biological sample contains cancerous cells, estimating the likelihood of a mammal developing cancer, and monitoring the efficacy of anti-cancer treatment in a mammal with cancer. Such methods are based on the discovery that cancer cells have an elevated level of Pellino 1 or 2 polynucleotide (i.e., gene copy number and/or mRNA) and/or polypeptide. Accordingly, by determining whether or not a cell contains elevated levels of Pellino 1 or 2 polynucleotide or polypeptide, it is possible to determine whether or not the cell is cancerous. Further, the presence of cancerous cells can be determined indirectly, i.e., in certain embodiments a biological sample that does not itself contain cancerous cells, but which has been taken from an animal with cancerous cells elsewhere in its body, may contain elevated levels of Pellino 1 or 2 reflecting the presence of the cancerous cells.

In numerous embodiments of the present invention, the level and/or presence of Pellino 1 or 2 polynucleotide or polypeptide will be detected in a biological sample, thereby detecting the presence or absence of cancerous cells in the biological sample, or, in certain embodiments, in the mammal from which the biological sample was removed. In preferred embodiments, the biological sample will comprise a tissue sample from a tissue suspected of containing cancerous cells. For example, in an individual suspected of having colon cancer, colorectal tissue is removed. Often, such methods will be used in conjunction with additional diagnostic methods, e.g., detection of other cancer markers, coloscopy, etc. In other embodiments, a tissue sample known to contain cancerous cells, e.g., from a tumor, will be analyzed for Pellino 1 or 2 levels to determine information about the cancer, e.g., the efficacy of certain treatments, the survival expectancy of the animal, etc.

The amount of Pellino 1 or 2 polynucleotide or polypeptide that will indicate the presence of a cancer will depend on numerous factors, including the type of cancer, the age, sex, medical history, etc., of the patient, the cell type, the assay format, etc. In some embodiments, a level of Pellino 1 or 2 in a biological sample will not be quantified or directly compared with a control sample, but will rather be detected relative to a "diagnostic presence" of Pellino 1 or 2, wherein a "diagnostic presence" refers to an amount of Pellino 1 or 2 polynucleotide or polypeptide that indicates the presence of cancer, or indicates a likelihood of cancer, in the mammal from which the sample was taken. Preferably, a "diagnostic presence" will be detectable in a simple assay giving a positive or negative result, where a positive "detection" of a "diagnostic presence" of Pellino 1 or 2 polynucleotide or polypeptide indicates the presence of cancer in the mammal.

The Pellino 1 or 2 level need not be quantified for a "diagnostic presence" to be detected, merely any method of determining whether Pellino 1 or 2 is present at levels higher than in a normal, cancer-free cell, sample, or mammal. In addition, a "diagnostic presence" does not refer to any absolute quantity of Pellino 1 or 2, but rather on an amount that, depending on the biological sample, cell type, assay conditions, medical condition of the mammal, etc., is sufficient to distinguish the level in a cancerous, or pre-cancerous sample, from a normal, cancer-free sample.

Such methods can be practiced regardless of whether any Pellino 1 or 2 polynucleotide or polypeptide is normally present, or "expected" to be present, in a particular control sample. For example, Pellino 1 or 2 may not be expressed in certain cell types, resulting in a complete absence of Pellino 1 or 2 in a control biological sample consisting of such cell types. For such biological sample, a "diagnostic presence" refers to any detectable amount of Pellino 1 or 2, using any assay. In other tissues, however, there may be a detectable level of Pellino 1 or 2 present in normal, cancer-free cells, and a "diagnostic presence" represents a level that is higher than the normal level, preferably representing a "statistically significant" increase over the normal level. Often, a "diagnostic presence" of Pellino 1 or 2 polynucleotide, polypeptide, and/or protein activity in a biological sample will be at least about 1.5, 2, 5, 10, or more fold greater than a level expected in a sample taken from a normal, cancer-free mammal.

Further, the present methods can be used to assess the efficacy of a course of treatment. For example, in a mammal with cancer from which a biological sample has been found to contain an elevated amount of Pellino 1 or 2 polynucleotide or polypeptide, the efficacy of an anti-cancer treatment can be assessed by monitoring, over time, Pellino 1 or 2 levels. For example, a reduction in Pellino 1 or 2 polynucleotide or polypeptide levels in a biological sample taken from a mammal following a treatment, compared to a level in a sample taken from the mammal before, or earlier in, the treatment, indicates efficacious treatment.

Determining a Prognosis

The level of Pellino 1 or 2 can be used to determine the prognosis of a mammal with cancer. For example, if cancer is detected using a technique other than by detecting Pellino 1 or 2, e.g., tissue biopsy, then the presence or absence of Pellino 1 or 2 can be used to determine the prognosis for the mammal, i.e., an elevated level of Pellino 1 or 2 will indicate a reduced survival expectancy in the mammal compared to in a mammal with cancer but with a normal level of Pellino 1 or 2. As used herein, "survival expectancy" refers to a prediction regarding the severity, duration, or progress of a disease, condition, or any symptom thereof. In a preferred embodiment, an increased level, a diagnostic presence, or a quantified level, of Pellino 1 or 2 is statistically correlated with the observed progress of a disease, condition, or symptom in a large number of mammals, thereby providing a database wherefrom a statistically-based prognosis can be made in view of any detected level or presence of Pellino 1 or 2. For example, in a particular type of mammal, i.e., a human of a particular age, gender, medical condition, medical history, etc., a detection of a level of Pellino 1 or 2 that is, e.g., 2 fold higher than a control level may indicate, e.g., a 10% reduced survival expectancy in the human compared to in a similar human with a normal level of Pellino 1 or 2, based on a previous study of the level of Pellino 1 or 2 in a large number of similar patients whose disease progression was observed and recorded.

The methods of the present invention can be used to determine the optimal course of treatment in a mammal with cancer. For example, the presence of an elevated level of Pellino 1 or 2 can indicate a reduced survival expectancy of a mammal with cancer, thereby indicating a more aggressive treatment for the mammal. In addition, a correlation can be readily established between levels of Pellino 1 or 2, or the presence or absence of a diagnostic presence of Pellino 1 or 2, and the relative efficacy of one or another anti-cancer agent. Such analyses can be performed, e.g., retrospectively, i.e., by detecting Pellino 1 or 2 levels in samples taken previously from mammals that have subsequently undergone one or more types of anti-cancer therapy, and correlating the Pellino 1 or 2 levels with the known efficacy of the treatment.

Treating Cancer

The present invention provides numerous methods for treating a mammal with cancer. In addition to allowing the determination of an optimal treatment for a mammal with cancer, as described supra, methods are provided for treating a cancer by inhibiting the growth, proliferation, or steroid hormone production of cells within the mammal, e.g., cancer cells. Typically, the methods are directed at reducing the level of Pellino 1 or 2 polypeptides, polynucleotides, or protein activity in a cancerous cell. It will be appreciated that more than one of the methods described infra can be performed on a given animal, and may also be administered in conjunction with one or more traditional, well known anti-cancer therapies, e.g., chemotherapy, radiation therapy, surgery, hormone therapy, immunotherapy, etc.

According to the present invention, a "method of treating cancer" refers to a procedure or course of action that is designed to reduce or eliminate the number of cancer cells in an animal, or to alleviate the symptoms of a cancer. "A method of treating cancer" does not necessarily mean that the cancer cells will, in fact, be eliminated, that the number of cells will, in fact, be reduced, or that the symptoms of a cancer will, in fact, be alleviated. Often, a method of treating cancer will be performed even with a low likelihood of success, but which, given the medical history and estimated survival expectancy of an animal, is nevertheless deemed an overall beneficial course of action.

In certain embodiments, the present invention provides methods for treating cancer by detecting the level and/or a diagnostic presence of Pellino 1 or 2 polynucleotide or polypeptide in a biological sample, and, when a diagnostic presence or increased level is detected, applying one or more anti-cancer therapies, including, but not limited to, chemotherapy, radiation therapy, surgery, immunotherapy, hormone therapy, and gene therapy.

One commonly applied anti-cancer therapy is chemotherapy, i.e., the administration of chemical compounds to a mammal with cancer that is aimed at killing or reducing the number of cancer cells within the mammal. Generally, chemotherapeutic agents arrest the growth of or kill cells that are dividing or growing, such as cancer cells. Examples of chemotherapeutic agents include, but are not limited to, genistein, taxol, busulfan, cisplatin, cyclophosphamide (cytoxan), dacarbazine, ifosfamide, mechlorethamine (mustargen), melphalan, carmustine, lomustine, 5-fluorouracil, methotrexate, gemcitabine, cytarabine (Ara-C), fludarabine, bleomycin, dactinomycin, daunorubicin, doxorubicin (Adriamycin), idarubicin, paclitaxel, docetaxel, etoposide, vinblastine, vincristine, vinorelbine, L-asparaginase, amsacrine, tretinoin, prednisone and dexamethasone.

Another commonly applied anti-cancer therapy is radiation therapy, wherein radioactivity is administered to a mammal with cancer. Radiation kills or inhibits the growth of dividing cells, such as cancer cells. The administration of radiation may be from an external source (e.g., a gamma source, a proton source, a molecular beam source, etc.), or may be through an implantable radioactive material, or a radioactive molecule such as an antibody.

In numerous embodiments, a tissue found to be cancerous using the present methods will be removed using surgery, i.e., the direct removal or ablation of cells, e.g., cancer cells, from a mammal. Most often, the cancer cells will be in the form of a tumor (e.g., a mammary tumor), which is removed from the mammal. The surgical methods may involve removal of healthy as well as cancerous tissue.

Hormone therapy can also be used to treat cancers, e.g., breast cancer. For example, compounds can be administered to a patient that counteract or inhibit hormones, such as estrogen or androgen, that have a mitogenic effect on cells and which often act to increase the cancerous properties of cancer cells in vivo. Hormone therapy can also include methods of reducing or eliminating the production of hormones in an animal, e.g., the surgical removal of ovaries in an animal to prevent estrogen production.

In certain embodiments, immunotherapy will be used to treat a cancer following a diagnosis based on detection of Pellino 1 or 2, i.e., methods of enhancing the ability of an animal's immune system to destroy cancer cells within the animal. Numerous such methods are well known to those of skill in the art. This can involve the treatment with polyclonal or monoclonal antibodies (e.g., Herceptin for treating breast cancer) that bind to particular molecules located on, produced by, or indicative of, tumor cells. Immunotherapeutic methods are well know to those of skill in the art (see, e.g., Pastan et al.(1992) *Ann. Rev. Biochem.*, 61: 331–354, Brinkman and Pastan (1994) *Biochimica Biphysica Acta*, 1198: 27–45, etc.).

In other embodiments, gene therapy will be used to treat a cancer diagnosed based on a detection of Pellino 1 or 2. In such embodiments, a nucleic acid is introduced into cells, e.g., cancer cells, to provide treatment for the cancer. Pellino 1 or 2 expression can be targeted or other cancer-associated genes can be targeted. For example, tumor suppressor genes that are often missing or mutated in a cancer cell, e.g., p53, RB, p21, p16, and others, can be replaced or overexpressed by introducing a nucleic acid encoding a functional gene into the cells. In addition, genes whose overexpression or increased activity contributes to cancer, e.g., ras, telomerase, etc., can be inhibited by any of a number of methods, including, but not limited to, antisense, ribozymes, and polynucleotides encoding dominant negative forms or other inhibiting polypeptides. Such nucleic acids can be delivered using any of a variety of methods, e.g., liposomal formulations, viral vectors, naked DNA injection, etc., and can be performed in vivo or ex vivo.

In preferred embodiments, this invention provides methods of treating a cancer by reducing Pellino 1 or 2 levels in a cell. Typically, such methods are used to reduce an elevated level of Pellino 1 or 2, e.g., an elevated level in a cancerous cell, and can be performed in any of a number of ways, e.g., lowering the copy number of the Pellino 1 or 2 gene or decreasing the level of Pellino 1 or 2 mRNA, protein, or protein activity in a cell. Preferably, the level of Pellino 1 or 2 activity is lowered to a level typical of a normal, cancer-free cell, but the level may be reduced to any level that is sufficient to decrease the proliferation or steroid production of the cell, including to levels above or below those typical of normal cells. Preferably, such methods involve the use of inhibitors of Pellino 1 or 2, where an "inhibitor of Pellino 1 or 2" is a molecule that acts to reduce Pellino 1 or 2 polynucleotide levels, Pellino 1 or 2 polypeptide levels and/or Pellino 1 or 2 protein activity. Such inhibitor s include, but are not limited to, antisense polynucleotides, ribozymes, antibodies, dominant negative Pellino 1 or 2 forms, and small molecule inhibitors of Pellino 1 or 2.

In preferred embodiments, Pellino 1 or 2 levels will be reduced so as to reduce the growth or proliferation of a cancer cell with elevated Pellino 1 or 2 levels. The proliferation of a cell refers to the rate at which the cell or population of cells divides, or to the extent to which the cell or population of cells divides or increases in number. Proliferation can reflect any of a number of factors, including the rate of cell growth and division and the rate of cell death.

The ability of any of the present compounds to affect Pellino 1 or 2 activity can be determined based on any of a number of factors, including, but not limited to, a level of Pellino 1 or 2 polynucleotide, e.g., mRNA or genomic DNA, the level of Pellino 1 or 2 polypeptide, the degree of binding of a compound to a Pellino 1 or 2 polynucleotide or polypeptide, Pellino 1 or 2 intracellular localization, or any functional properties of Pellino 1 or 2 protein.

Inhibitors of Pellino 1 or 2 Polynucleotides

Antisense Polynucleotides

In certain embodiments, Pellino 1 or 2 activity is down-regulated, or entirely inhibited, by the use of antisense polynucleotide, i.e., a nucleic acid complementary to, and which can preferably hybridize specifically to, a coding mRNA nucleic acid sequence, e.g., Pellino 1 or 2 mRNA, or a subsequence thereof. Binding of the antisense polynucleotide to the Pellino 1 or 2 mRNA reduces the translation and/or stability of the Pellino 1 or 2 mRNA.

In the context of this invention, antisense polynucleotides can comprise naturally-occurring nucleotides, or synthetic species formed from naturally-occurring subunits or their close homologs. Antisense polynucleotides may also have altered sugar moieties or inter-sugar linkages. Exemplary among these are the phosphorothioate and other sulfur containing species which are known for use in the art. All such analogs are comprehended by this invention so long as they function effectively to hybridize with Pellino 1 or 2 mRNA.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Ribozymes

In addition to antisense polynucleotides, ribozymes can be used to target and inhibit transcription of Pellino 1 or 2. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto et al. (1994) *Adv. in Pharmacology* 25: 289–317 for a general review of the properties of different ribozymes).

The general features of hairpin ribozymes are described, e.g., in Hampel et al. (1990) *Nucl. Acids Res.* 18: 299–304; Hampel et al. (1990) European Patent Publication No. 0 360 257; U.S. Pat. No. 5,254,678. Methods of preparing are well known to those of skill in the art (see, e.g., Wong-Staal et al., WO 94/26877; Ojwang et al. (1993) *Proc. Natl. Acad. Sci. USA* 90: 6340–6344; Yamada et al. (1994) *Human Gene Therapy* 1: 39–45; Leavitt et al. (1995) *Proc. Natl. Acad. Sci. USA* 92: 699–703; Leavitt et al. (1994) *Human Gene Therapy* 5: 1151–120; and Yamada et al. (1994) *Virology* 205: 121–126).

Inhibitors of Pellino 1 or 2 Polypeptide Activity

Pellino 1 or 2 activity can also be decreased by the addition of an inhibitor of the Pellino 1 or 2 polypeptide. This can be accomplished in any of a number of ways, including by providing a dominant negative Pellino 1 or 2 polypeptide, e.g., a form of Pellino 1 or 2 that itself has no activity and which, when present in the same cell as a functional Pellino 1 or 2, reduces or eliminates the Pellino 1 or 2 activity of the functional Pellino 1 or 2. Design of dominant negative forms is well known to those of skill and is described, e.g., in Herskowitz (1987) *Nature* 329(6136): 219–22. Also, inactive polypeptide variants (muteins) can be used, e.g., by screening for the ability to inhibit Pellino 1 or 2 activity. Methods of making muteins are well known to those of skill (see, e.g., U.S. Pat. Nos. 5,486,463, 5,422,260, 5,116,943, 4,752,585, 4,518,504). In addition, any small molecule, e.g., any peptide, amino acid, nucleotide, lipid, carbohydrate, or any other organic or inorganic molecule can be screened for the ability to bind to or inhibit Pellino 1 or 2 activity, as described below.

Screening for Pellino 1 or 2 Inhibitors

Pellino 1 or 2 and its variants are proteins that participate in cellular processes such as proliferation and chromosomal segregation. The activity of Pellino 1 or 2 polypeptides can be assessed using a variety of in vitro and in vivo assays to determine functional, chemical, and physical effects, e.g., cellular proliferation, and the like. Furthermore, such assays can be used to test for inhibitors and activators of Pellino 1 or 2. Modulators can also be genetically altered versions of an Pellino 1 or 2. Screening assays of the invention are used to identify modulators that can be used as therapeutic agents, e.g., antibodies to Pellino 1 or 2 and inhibitors of Pellino 1 or 2 activity.

In one embodiment, this invention provides methods of screening for agents that modulate and preferably down-regulate Pellino 1 or 2 protein activity. Preferred "screening" methods of this invention involve (i) contacting a Pellino 1 or 2- expressing cell (e.g., a cell capable of expressing Pellino 1 or 2) with a test agent; and (ii) detecting the level of Pellino 1 or 2 activity (e.g., as described above), where a decreased level of Pellino 1 or 2 activity as compared to the level of Pellino 1 or 2 activity in a cell not contacted with the test agent indicates that the test agent inhibits or downregulates Pellino 1 or 2.

The Pellino 1 or 2 of the assay is typically a polypeptide having a sequence of SEQ ID NO:2 or 4 or a conservatively modified variant thereof or a Pellino polypeptide as defined in the definition section herein. Optionally, the polypeptide of the assays will comprise a domain of an Pellino 1 or 2. Either a Pellino 1 or 2 or a domain thereof can be covalently linked to a heterologous protein to create a chimeric protein used in the assays described herein.

Modulators of Pellino 1 or 2 activity are tested using Pellino 1 or 2 polypeptides as described above, either recombinant or naturally occurring. The protein can be isolated, expressed in a cell, expressed in a membrane derived from a cell, expressed in tissue or in an animal, either recombinant or naturally occurring. For example, colon cancer cells, or proliferating cells can be used. Inhibition is tested using one of the in vitro or in vivo assays described herein. Gene amplification can also be examined. Furthermore, ligand-binding domains of the protein, e.g., an ATP binding domain, of interest can be used in vitro in soluble or solid state reactions to assay for ligand binding.

Activity of Pellino 1 or 2 or a domain thereof, can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

Samples or assays that are treated with a potential Pellino 1 or 2 inhibitor are compared to control samples without the test compound, to examine the extent of modulation. Control samples that are not treated with the test inhibitor are assigned a relative Pellino 1 or 2 activity value of 100. Inhibition of Pellino 1 or 2 is achieved when the Pellino 1 or 2 activity value relative to the control is about 90%, optionally 50%, optionally 25–0%.

Modulators of Pellino 1 and 2

The compounds tested as modulators of Pellino 1 or 2 include, but are not limited to, natural or synthetic nucleic acids, natural or synthetic polypeptides, natural or synthetic lipids, natural or synthetic small organic molecules, and the like. Alternatively, modulators can be genetically altered versions of an Pellino 1 or 2. Typically, test compounds will be small chemical molecules and peptides. Essentially any chemical compound can be used as a potential modulator or ligand in the assays of the invention, although most often compounds can be dissolved in aqueous or organic (especially DMSO-based) solutions. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred format, test agents are provided as members of a combinatorial library. In preferred embodiments, a collection of small molecule inhibitors are tested for Pellino 1 or 2 inhibiting ability. A "small molecule inhibitor" of Pellino 1 or 2 is any molecule, e.g., a carbohydrate, nucleotide, amino acid, oligonucleotide, oligopeptide, lipid, inorganic compound, etc. that inhibits Pellino 1 or 2 protein activity. Such molecules can inhibit Pellino 1 or 2 protein activity by any of a number of mechanisms, e.g., by binding to a Pellino 1 or 2 protein and competitively inhibiting the ATPase function or the ability to bind ATP. Preferably, such "small molecule inhibitors" are smaller than about 10 kD. More preferably, such inhibitors are smaller than about 5, 2, or 1 kD or less.

As discussed above, test agents can be screened based on any of a number of factors, including, but not limited to, a level of Pellino 1 or 2 polynucleotide, e.g., mRNA or genomic DNA, the level of Pellino polypeptide, the degree of binding of a compound to a Pellino 1 or 2 polynucleotide or polypeptide, Pellino 1 or 2 intracellular localization, or any functional properties of Pellino 1 or 2 protein. Such direct and indirect measures of Pellino 1 or 2 activity in vivo can readily be used to detect and screen for molecules that modulate Pellino 1 or 2 activity.

Combinatorial Libraries

In certain embodiments, combinatorial libraries of potential Pellino 1 or 2 modulators will be screened for an ability to bind to a Pellino 1 or 2 polypeptide or to modulate Pellino 1 or 2 activity. Conventionally, new chemical entities with useful properties are generated by identifying a chemical compound (called a "lead compound") with some desirable property or activity, e.g., Pellino 1 or 2 inhibiting activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Millions of chemical compounds can be synthesized through such combinatorial mixing of chemical building blocks (Gallop et al. (1994) *J. Med. Chem.* 37(9): 1233–1251).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37: 487–493, Houghton et al. (1991) *Nature,* 354: 84–88), peptoids (PCT Publication No WO 91/19735, Dec. 26, 1991), encoded peptides (PCT Publication WO 93/20242, Oct. 14, 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083), antibody libraries (see, e.g., Vaughn et al (1996) *Nature Biotechnology,* 14(3): 309–314), and PCT/US96/10287), carbohydrate libraries (see, e.g., Liang et al., (1996) *Science,* 274: 1520–1522, and U.S. Pat. No. 5,593,853), and small organic molecule libraries (see, e.g., benzodiazepines, Baum (1993) C&EN, Jan 18, page 33; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

High Throughput Screening

Any of the assays to identify compounds capable of modulating Pelliono levels described herein are amenable to high throughput screening. Preferred assays thus detect enhancement or inhibition of Pellino 1 or 2 gene transcription, inhibition or enhancement of Pellino 1 or 2 polypeptide expression, and inhibition or enhancement of Pellino 1 or 2 polypeptide activity.

High throughput assays for the presence, absence, quantification, or other properties of particular nucleic acids or protein products are well known to those of skill in the art. Similarly, binding assays and reporter gene assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass; Air Technical Industries, Mentor, Ohio; Beckman Instruments, Inc. Fullerton, Calif.; Precision Systems, Inc., Natick, Mass., etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Computer-assisted Identification of Inhibitors of Pellino 1 or 2

Another assay for compounds that modulate or inhibit Pellino 1 or 2 activity involves computer assisted drug design, in which a computer system is used to generate a three-dimensional structure of Pellino 1 or 2 based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering protein amino acid sequences of at least 10 amino acid residues or corresponding nucleic acid sequences encoding a Pellino 1 or 2 polypeptide into the computer system. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of Pellino 1 or 2 to identify ligands that bind to Pellino 1 or 2. Binding affinity between the protein and ligands is determined using energy terms to determine which ligands have an enhanced probability of binding to the protein.

Computer systems are also used to screen for mutations, polymorphic variants, alleles and interspecies homologs of Pellino 1 or 2 genes. Such mutations can be associated with disease states or genetic traits. As described above, Gene-Chip™ and related technology can also be used to screen for mutations, polymorphic variants, alleles and interspecies homologs. Once the variants are identified, diagnostic assays can be used to identify patients having such mutated genes. Identification of the mutated Pellino 1 or 2 genes involves receiving input of a first nucleic acid or amino acid sequence encoding Pellino 1 or 2. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in Pellino 1 or 2 genes, and mutations associated with disease states and genetic traits.

Administration of Pellino 1 or 2 -Inhibiting Compounds

In numerous embodiments of the present invention, a Pellino 1 or 2 inhibiting compound, i.e., a compound that reduces levels of Pellino 1 or 2 mRNA, polypeptide and/or protein activity, will be administered to an animal. Such compounds can be administered by a variety of methods including, but not limited to, parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include, but are not limited to, powder, tablets, pills, capsules and lozenges. It is recognized that Pellino 1 or 2 modulators (e.g., antibodies, antisense constructs, ribozymes, small organic molecules, etc.) when administered orally, must be protected from digestion. This is typically accomplished either by complexing the molecule(s) with a composition to render it resistant to acidic and enzymatic hydrolysis, or by packaging the molecule(s) in an appropriately resistant carrier, such as a liposome. Means of protecting agents from digestion are well known in the art.

The compositions for administration will commonly comprise a Pellino 1 or 2 inhibitor dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing inhibitors of Pellino 1 or 2 can be administered for therapeutic or prophylactic treatments. In therapeutic applications, compositions are administered to a patient suffering from a disease (e.g., a cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of a Pellino 1 or 2 modulator that is capable of preventing or slowing the development of cancer in a mammal is referred to as a "prophylactically effective dose." The particular dose required for a prophylactic treatment will depend upon the medical condition and history of the mammal, the particular cancer being prevented, as well as other factors such as age, weight, gender, etc. Such prophylactic treatments may be used, e.g., in a mammal who has previously had cancer to prevent a recurrence of the cancer, or in a mammal who is suspected of having a significant likelihood of developing cancer.

It will be appreciated that any of the present Pellino 1 or 2-inhibiting compounds can be administered alone or in combination with additional Pellino 1 or 2-inhibiting compounds or with any other therapeutic agent, e.g., other anti-cancer agents or treatments.

In numerous embodiments, one or more nucleic acids, e.g., Pellino 1 or 2 polynucleotides, such as antisense polynucleotides or ribozymes, will be introduced into cells, in vitro or in vivo. The present invention provides methods, reagents, vectors, and cells useful for expression of Pellino 1 or 2 and other polypeptides and nucleic acids using in vitro (cell-free), ex vivo or in vivo (cell or organism-based) recombinant expression systems.

The particular procedure used to introduce the nucleic acids into a host cell for expression of a protein or nucleic acid is application specific. Any of the well known procedures for introducing foreign nucleotide sequences into host cells may be used. These include the use of calcium phosphate transfection, spheroplasts, electroporation, liposomes, microinjection, plasma vectors, viral vectors and any of the other well known methods for introducing cloned genomic DNA, cDNA, synthetic DNA or other foreign genetic material into a host cell (see, e.g., Berger and Kimmel, *Guide to Molecular Cloning Techniques, Methods in Enzymology* volume 152 Academic Press, Inc., San Diego, Calif. (Berger), F. M. Ausubel et al., eds., Current Protocols, a joint venture between Greene Publishing Associates, Inc. and John Wiley & Sons, Inc., (supplemented through 1999), and Sambrook et al., *Molecular Cloning—A Laboratory Manual* (2nd Ed.), Vol. 1–3, Cold Spring Harbor Laboratory, Cold Spring Harbor, N.Y., 1989.

In numerous embodiments of this invention, nucleic acids encoding Pellino polypeptides, or inhibitors thereof, will be inserted into vectors using standard molecular biological techniques. Vectors may be used at multiple stages of the practice of the invention, e.g., for subcloning nucleic acids encoding Pellino 1 or 2 polypeptides or Pellino 1 or 2 inhibitors, e.g., Pellino 1 or 2 ribozymes or antisense sequences, or for subcloning additional elements used to control protein or mRNA expression, vector selectability, etc. Vectors may also be used to maintain or amplify the nucleic acids, for example, by inserting the vector into prokaryotic or eukaryotic cells and growing the cells in culture. In addition, vectors may be used to introduce and express Pellino 1 or 2 nucleic acids, or Pellino 1 or 2 -inhibiting nucleic acids, e.g., Pellino 1 or 2 ribozymes or antisense sequences, into cells for therapeutic or experimental purposes.

A variety of commercially or commonly available vectors and vector nucleic acids can be converted into a vector of the invention by cloning a polynucleotide of this invention into the commercially or commonly available vector. A variety of common vectors suitable for this purpose are well known in the art. For cloning in bacteria, common vectors include pBR322-derived vectors such as pBLUESCRIPT™, and bacteriophage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

Typically, a nucleic acid subsequence encoding a Pellino 1 or 2 polypeptide is placed under the control of a promoter. A nucleic acid is "operably linked" to a promoter when it is placed into a functional relationship with the promoter. For instance, a promoter or enhancer is operably linked to a coding sequence if it increases or otherwise regulates the transcription of the coding sequence. Similarly, a "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include promoters and, optionally, introns, polyadenylation signals, and transcription termination signals. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

An extremely wide variety of promoters are well known, and can be used in the vectors of the invention, depending on the particular application. Ordinarily, the promoter selected depends upon the cell in which the promoter is to be active. Other expression control sequences such as ribosome binding sites, transcription termination sites and the like are also optionally included. For *E. coli*, example control sequences include the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, a retrovirus (e.g., an LTR based promoter) etc., and a polyadenylation sequence, and may include splice donor and acceptor sequences.

Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, Pellino 1 or 2 specific nucleic acids or antibodies, hybridization probes and/or primers, antisense polynucleotides, ribozymes, dominant negative Pellino 1 or 2 polypeptides or polynucleotides, small molecules inhibitors of Pellino 1 or 2, etc. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The present invention also provides for kits for screening for inhibitors of Pellino 1 or 2. Such kits can be prepared from readily available materials and reagents. For example, such kits can comprise any one or more of the following materials: a Pellino 1 or 2 polypeptide or polynucleotide, reaction tubes, and instructions for testing Pellino 1 or 2 activity. Optionally, the kit contains biologically active Pellino 1 or 2. A wide variety of kits and components can be prepared according to the present invention, depending upon the intended user of the kit and the particular needs of the user.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Cloning of Pellino 2

Four nano-grams of Clontech Human Universal Quick-Clone cDNA (product # 7109-1) was mixed in a total volume of 50 µL with these ingredients: 200 µM dNTP, oligonucleotides PELD1 and PELD2 (PELD1=ATGTTTTCCCCTGGCCAGGAGGAACAC (SEQ ID NO:5), PELD2=TCAGTCAATTGGACCTTGGAAAATTAA (SEQ ID NO:6); 0.5 µM each), 20 mM Tris-HCl pH 8.85, 6m M $(NH_4)_2S_4$, 10m M KCl, 2 mM $MgSO_4$, 0.1% Triton-X-100, 10 µg/mL nuclease-free bovine serum albumin, and 3 units of pfu-turbo DNA polymerase (Stratagene, La Jolla, Calif.). The reaction was then overlaid with mineral oil (30 µL ) and amplified using a PCR thermal cycler (MJ Research, Watertown, Mass.) for 40 cycles where each cycle consists of 3 steps: 950°C. for 20 sec, 59° C. for 30 sec, and 72° C. for 1.5 min. Subsequently, the mixture was purified using High-Pure PCR purification columns (Roche, Indianapolis, Ind.) following manufacturer's recommendation. Upon analyses using 2% agarose gel electrophoresis, a product of approximately 1.3 kb in length was detected, representing the full-length open reading frame of Pellino-2.

Example II

Amplification and Overexpression of Pellino 2 Gene in Cancer Cells

FIG. 2 summarizes the expression status of Pellino-2 mRNA in various lung cancer cell lines. The method, RT-QPCR, was used to generate the data therein. In brief, total RNA was isolated from tumor cell lines using the Trizol reagent (Gibco/Life technology, Gaithersburg, Md.) and stored in RNAsecure (Ambion, Austin, Tex.). Total RNA was treated with DNA-free reagents (Ambion) to eliminate contaminating genomic DNA and then subjected to reverse transcriptase reaction coupled with PCR amplification in a one-tube format according to the manufacturer using the Taqman 7700 sequence detector (Applied Biosystems, Foster city, Calif.). The numbers of PCR cycles needed to cross a preset threshold, also known as Ct value, in the sample tumor RNA preps and in the RNA preps from a series of human placenta RNA at various concentrations were measured for both the target probe (i.e., Pellino-2) and the β-actin probe. The relative abundance of target sequence to β-actin in each sample was then calculated by statistical analyses of the Ct values of the unknown samples and the standard curve generated from a series of human placental RNA preps of various concentrations.

To determine the overexpression level relative to normal background, the ratios of target probe over β-actin in tumors were normalized to the ratio in normal human bronchial epithelial cells (Clonetics/Cambrex Products). Pellino-2 is very highly overexpressed (>1000 fold) in 5 out of 10 lung cell lines, indicating that Pellino-2 overexpression is advantageous for lung tumor cell growth (see FIG. 2). Overexpression does not appear to be limited to a particular tumor type.

Example II

Amplification of Pellino 2 Gene in Cancer Cells

FIG. 3 summarizes the Pellino-2 gene copy number in various tumors and tumor cell lines. These results were obtained using the quantitative PCR (QPCR) technique. Briefly, probe to Pellino-2 3' untranslated region was designed using PrimerExpress software (Applied Biosystems). This probe set consisting of 3 oligonucleotides (N63226QF: GATGCTGAAGTCGTCTCATTGG (SEQ ID NO:7), N63226QR: CCAGTAGTTTAGCCTTTGTGGCTT (SEQ ID NO:8), N63226QP: [6-FAM]-CGCACAGAAG-GAGGCGCATCATAAC-[TAMRA] (SEQ ID NO:9)) was purchased from Operon Technologies (Alameda, Calif.). Following manufacturer's protocol and the standard curve method as described for FIG. 2, the Pellino-2 probe and a reference probe set (TLF7QF: GGTCTCTATTTGCACT-TGGCTGAT (SEQ ID NO:10), TLF7QR: TTTTCATTGT-TGACCAAGCTAGACA (SEQ ID NO:11), TLF7QP: [6-FAM]-TAGGGCATACTGCCTGCATATTTCCTGCT-[TAMRA] (SEQ ID NO:12)) representing single copy region in the human genome were used to determine the Pellino-2 gene copy number in tumor DNAs using Taqman 7700 sequence detector (Applied Biosytems).

FIG. 3 lists the Pellino-2 gene DNA copy number in various tumor and tumor cell line genomes. A cutoff of 2.5 fold is used to differentiate amplified (>2.5×) versus non-amplified (<2.5×) tumors. Amplification frequency is calculated by dividing the number of amplified tumors over the total number of tumors screened for a given tumor type.

What is claimed is:

1. A method of detecting epithelial cancer cells in a biological sample from a mammal, the method comprising the steps of:
   (a) providing the biological sample from the mammal; and
   (b) detecting an increase in copy number of a gene encoding SEQ ID NO:4 in the biological sample compared to control, thereby detecting the presence of epithelial cancer cells in the biological sample.

2. The method of claim 1, wherein the detecting step further comprises:
   (i) contacting the gene with a probe specific for the gene under conditions in which the probe selectively hybridizes to the gene to form a stable hybridization complex; and
   (ii) detecting the hybridization complex.

3. The method of claim 1, wherein the epithelial cancer is a lung, colon, or ovarian cancer.

4. The method of claim 1, wherein the mammal is a human.

* * * * *

SEQUENCE LISTING

```
<160> NUMBER OF SEQ ID NOS: 42

<210> SEQ ID NO 1
<211> LENGTH: 7136
<212> TYPE: DNA
<213> ORGANISM: Homo sapiens
<220> FEATURE:
<223> OTHER INFORMATION: human pellino 1 cDNA
<220> FEATURE:
<221> NAME/KEY: CDS
<222> LOCATION: (4039)..(5295)
<223> OTHER INFORMATION: human pellino 1

<400> SEQUENCE: 1
gcttatattt tttccagctc ccaaattccc tttattccac tttagtccct tcattttcag      60
agatgaggaa acagattgct ttgttcaaag acagctagaa ctagaacaca ggctaatact     120
tgctagccat gtgatatact aatgtcagcc aaatacgggc atttacactt tcagatgttt     180
gccatatctg tgcacttact aattctgttt aatacaattt aaattgactc ctttaaataa     240
gcttatttta aaggaaattt tttgctacta taaatagaaa accattatat cctttaaata     300
gtaactctaa ataggaattc aaaacaaagc aacgttatta aaatttaatt taaaattaat     360
ttaaatttaa ttgttattaa atttttaatt attgctgttc ttcgtcagaa atgtgtcaaa     420
```

-continued

```
gcattgtttt catgtttgat gtcagttcct taattgtcta aacagaaaaa gcacagctaa     480
tgcctctagt taagcttctg tataactttt ttaaatgaaa tgcttcttag aggggaaatg     540
agagggcatg aatacatgtt tatatactaa agtatgattt catgtatatc agaagatctt     600
attatatgga accaaaatta ttctttggtt gatttaattg ttcttgaaac ttcagttttt     660
accttgaagg ttttagttag cttagcataa gtttattttt ctaaataagg aatctgattg     720
cctcacaact cagatgtatc acagttatgg tgaaatagca atatattggt ttctgtaacc     780 tttaaatac cgtaatgaat taaaatctct tcagcaaaag caaatatatc tagggtgacg      840
agaggtgttt ttagtgtatt tgaatgatgg aaatgttttt cttaaaatat ttctgaagca     900 tttttttaaaa taattttttg aatttattga tgatagtagt tgtgtgttag tgtgaatgac    960
tggtctaaat gtgtatgtca cttccaaggg attagtaggg gtcagaatga tttgttttat    1020
tcattgactt ttcctttgac gtgttcttat tcattgggct acatacattc cctgttgcct    1080
tctcaccaaa agtgccacta cacaggctgt atttcattgt actgtagaaa aagacaagta    1140
gacctttttc attcatgaga ttcctatgaa atctgttggt ggaggtataa aatgaggaga    1200
cttttatggg ctagctagta ggagttttgc tgtgaaacct ttgtaacagg tctatcagga    1260
actagggaga gaaataaatg caggaaatac ttgatcccat taaactgagg atgaaaaga    1320 catgataata ttttggggat tatttattgt gtgattttcc ggctgatcag aagtgttaat    1380
tttttgttat acttgtgtca aatacatata tatatatata ttttgaaatg gagtcttgct    1440
ctgtcaccca ggctggagtg cagtggtgcg atctgggttc actgcaacct ctgcctccag    1500
gttcaagtga tcctcctgcc tcagcctccc gagtagctag gactacaggc acgtgccacc    1560
acgccctgct aattttttgta ttcttagtgg agatggggtt tcaccatgtt ggccaggctg    1620
gtcttgaact cctgacctca agtgatcttc ccaccttggc ctttctgaac tatttccttt    1680
acacacattt agaactacat ctaactgtat tatagttttc actttcacca tcagacaaaa    1740
ttcagaagat tcaagagaag gaaagtcgat tgtatttact catattttg ctaccgtgtt     1800 tttacatctc atattttaag gctctcttaa ttatttattt tctgtttagt taatttcctc    1860
tagccattct ttatttatag tgggtctgct ggtaacaaat tctctcaatt tttcctcgtc    1920
tgagaatgtc ttgacttccc ttccattttt gtcagcacct gaaaaatact atgccactat    1980
cttctgggtt ctgtggtttc tgatgagaac tccactgtca gtctaattgt cgttataaat    2040
gcagtgttct ctctctctct ctgcttccag gatatttttt cttttttttt tttttttt     2100 tcttgagacg gagtctcact ctgtcgccca ggctggagtg cagtggcgca attttggctc    2160
actgcaagct ctgcctcccg ggttcaagcg attactccca ctttagcctc ccaagtagct    2220
aggactacaa ggcacaccac catgcctggc taatttttgt attttagta gagacggggt    2280 ttcaccatgt tgcccaggct ggtctcgaac tcctgacatc aagtgatctt cctgcctccg    2340
cttcccaaag tgctggaatt acaggcgtga gccactgctc ccagcctctt tatttttca    2400 gctttactct ttcttctgtc tttttgacat gtgtgtccag tgacacacgt gttagatttt    2460
gctatagtct cacgcacggg tctataaggc tctgtttttt gtttcatttt gttttttccta   2520 ttttctctct attcagatcg agtaatttcc actgttcagt tttatcatag ctgcttttaa    2580
atctttgtca ggtaattctg tcatctaagt tttggcacct attgattatc ttttgcattg    2640
tttttgtttt tgtttctgtt tttgttttga gatggagtct tgctctgttg cccaggttgg    2700
agtgcagtgg cactgatctc ggctcactgc aacctcctcc tcccgggttc aagtggttct    2760
cctgcctcaa cctccttagt agctgggatt acaggcatgt gccaccacgc ccggctaatt    2820
```

```
ttgtattttt agtagagacc aggtttatcc atgttggtca ggctggtctc aaactcccaa    2880
cctcaagtga tccgcctgcc tcgacctccc aaagtgctgg gattacaggc gtgaaccact    2940
gcacccagcc tatcttttgc attgttttaa atcttgttct tgctaggatg aatgattttc    3000
tgttaaaact agatattttc atattatgtt cctaggctct ggatattatc taaaccttct    3060
gtttccactg gcttttattg acactgcttt ggcaaggtca tagggggtgc ctcattactg    3120
ccaggtggac atagaagtca agggtcccta ctcagcctct actgatgcct caggaagagg    3180
atccttcttg ttattgctgg gtgggggtgg aagtctagct gacacctact gaggtaggtg    3240
ctggggcatg cccggccatc agggtgaaag tcctggctcc ctagttggcc tactttaca    3300 ttgccctaat agggcattgg agctcctcac tatggtttat gagctggaag tcaaggctcc    3360
tcacttagct ttcgttggtg tgggtggtgg tggggcaaaa ctgttttctg ggtttggctg    3420
gagtggagca gttactgtca aaagttttct gtcttgccag gctgtccctt tcttgtttct    3480
ttggctagag agagcaagct tttgttgtgg ctcttttttgt ctgtgccagt tggcatttcc    3540
aggttgctgc cttctttagc tccaagtctg ggatatatta ggcaaaaaga aaacccagag    3600
aatttacacc accgtgtcat tccatgggtc ctgaggtccc ttacttagtc tgccttctct    3660
ccacttttca cagtcttctc atgttttgta tataatgtcc agggtcttta gttatactta    3720
gcagaaataa aagggaaaag tatgtctgct ctatgcttct gtaagtggaa gtcttcaaat    3780
ttgcattttt gattcctta aacagttttg taaaatatat aatcattatt gggcaaaatg    3840
tcccataaaa tgtatatacc ttgtgatggt ttgcataata ttgtgttcaa gaggactgct    3900
gaaaaataac atctttattt aaactgaaac gaattgttca cattattaat gaaaactttt    3960
cccctctagg aaataatgca aaggtgtcc caaggctcct gaccagtgaa caaagatttg    4020
agaaagacag ccaagctcat gttttctcct gatcaagaaa atcatccatc taaagcacca    4080
gtaaaatatg gtgaactcat tgtcttaggc tataatgggt ctctcccaaa tggcgataga    4140
ggaaggagga aaagtaggtt tgctttgttt aaaagaccta aggcaaatgg ggtgaagccc    4200
agcactgtgc atattgcttg tactcctcag gctgcaaagg caataagcaa caaagaccag    4260
catagcatat catatacttt gtctcgggcc cagactgtgg tggttgaata tactcatgac    4320
agcaacacag atatgtttca gattggccgg tcgactgaaa gccccattga ttttgtagta    4380
actgacacgg ttcctggaag tcaaagtaat tctgatacac agtcagtaca aagcactata    4440
tcaagatttg cctgcagaat catatgtgaa cggaatcctc cctttacagc acggatttat    4500
gctgcaggat ttgactcatc aaaaaacatc tttcttgggg agaaggctgc caaatggaag    4560
acatcagatg gacagatgga tggcttgacc actaatggtg ttcttgtgat gcatccacgc    4620
aatgggttca cagaagactc caagcctgga atatggagag aaatatcggt gtgtggaaat    4680
gtatttagcc tacgtgaaac cagatcggct cagcagagag aaaaatggt ggaaattgaa    4740 accaatcagt tacaagatgg ctcgttaatt gacctctgtg gtgcaacatt gttatggcgt    4800
actgcagaag gcctttccca cactcctacc gtgaagcatt tagaagcttt aagacaggaa    4860
atcaatgcag cacgacctca gtgccctgta gggttcaaca cactagcatt tcctagtatg    4920
aagaggaaag acgttgtaga tgaaaaacaa ccatgggtat atctaaactg cggccatgta    4980
catggctatc ataactgggg aaacaaagaa gaacgtgatg gaaaagatcg tgaatgtcct    5040
atgtgtaggt ctgttggtcc ctatgttcct ctgtggcttg gatgtgaagc tggatttttat    5100 gtggacgccg gccctccaac ccatgcgttt agcccgtgtg ggcatgtgtg ttcagaaaag    5160
```

| | | |
|---|---|---|
| acaactgcct attggtccca gatcccactt cctcatggta ctcatacttt tcatgcagcc | 5220 |
| tgtccctttt gtgcacatca gttggctggt gaacaaggct acatcagact tatttttcaa | 5280 |
| ggacctctag actaacagac cattgtcttg caggactaca ttataaattt ataagctaag | 5340 |
| tgagttgggt tttcgaacct gttgtccacg tcacagtttt tctgctctgg tcatttgcat | 5400 |
| taagatgaag aatttttta aacatttata ataaatagta gcaatttctg agcaaaaatc | 5460 |
| tgggaaactc aagcaaagga atttctgaaa gtatcagtct tctgaattct gagttttgaa | 5520 |
| aatatatttt gaggagaaaa agacatagtc taatttgatg ccttccttt agtgttttg | 5580 |
| aatcacctat cctcagtgct gaaattgttt tgtataactg agggtactgt tggttcaaac | 5640 |
| tatgttagtt tacagtttgt tgcaaacatt gtaaataca gcgacatgta tattaacttt | 5700 |
| tttctattta tctttattat agaaaatacc ttagaatgtt cttgatagag tagcatggta | 5760 |
| acgatggtgt cacacccttg gtgtgaatgg tagcttagtg agcaacctag ctcaaggatt | 5820 |
| tgcaaagtta ggaagaagga cgagagagcc tctctcccca ccccaatcta aatatggaat | 5880 |
| ttggtaaatt agaatacttt gtaatttgta agaccaaatt catactaatt acccgcgtga | 5940 |
| aaggtgtttg tttttaacaa cattgaagat aatcaggaaa gattttttct taatgtttct | 6000 |
| ctcgagcgta gtactataac aaaaacttaa tgctaagaaa catttatat gctcctttgg | 6060 |
| atatgcaatt taatctagat tatctatttt tctcccatga taactaatct gtttttagta | 6120 |
| tcagcagcat ttggcaagtt tatttttgg atataaactg tggttcatct gttcactgtt | 6180 |
| tctagaaaaa aatcattgcc ataagaaaaa gtataaatta gcaagaaagg agagtgactt | 6240 |
| gatttgcttt tggaaaaaga aatgcttaat taattattct gtatttggcc ttattcgggc | 6300 |
| attaggaaat ctagagatct aaagggttga atgacaatag tgcccccgtt tttagcagac | 6360 |
| cagccttaac tctgggtttg aatcctaagg agattgccac agtgagactt aaggaaatgt | 6420 |
| ttggttggca gatgagcacc aatgactgca gcgtggagtg acgcactgca tggtctgttt | 6480 |
| attctctaat tccaatatgt cttttgcttc cagaagcaag aaaagtttct tctctcccct | 6540 |
| ccttcccacc cttttttcaa aggcaccaca agtatagaca gttgcactac atcaaatctt | 6600 |
| tttttgacac ttgtagaaac cagtacactt ttagattaga cagtatcttc ttttaatatt | 6660 |
| ttgatttgtt ttcctttagt ttgaaaagtt gtataatact taactgactg tagcaaagtt | 6720 |
| ttatatgtgg tagcatacct ttaatttatc ctattacaaa actgttctga atttttcttt | 6780 |
| ggttttaaa aaacaaaact tgttgcttag aagccatgaa ttattttatt ttacttcaac | 6840 |
| tgtcgaaact tccttgtttt aaaaaatgat catttgggtt cactcaggaa atgcatgtca | 6900 |
| ggaaacttgt attataagtt tattagttgt gatgtatcag taactgctgt tacccctttt | 6960 |
| tcaaagaaat gtaattgatt tgaagtttt ctagattgtc acatgctttg tgactaatgc | 7020 |
| aagaaagcaa gtcctgtgtt gtatttgttc tagtcatttt tattcaggct atatattgta | 7080 |
| gcttaatttt tatttgcaat taatttattt aaactaagta aatactttc aaaata | 7136 |

<210> SEQ ID NO 2
<211> LENGTH: 418
<212> TYPE: PRT
<213> ORGANISM: Homo sapiens
<220> FEATURE:
<223> OTHER INFORMATION: human pellino 1

<400> SEQUENCE: 2

Met Phe Ser Pro Asp Gln Glu Asn His Pro Phe Lys Ala Pro Val Lys
 1               5                  10                  15

-continued

```
Tyr Gly Glu Leu Ile Val Leu Gly Tyr Asn Gly Ser Leu Pro Asn Gly
             20                  25                  30

Asp Arg Gly Arg Arg Lys Ser Arg Phe Ala Leu Phe Lys Arg Pro Lys
         35                  40                  45

Ala Asn Gly Val Lys Pro Ser Thr Val His Ile Ala Cys Thr Pro Gln
     50                  55                  60

Ala Ala Lys Ala Ile Ser Asn Lys Asp Gln His Ser Ile Ser Tyr Thr
 65                  70                  75                  80

Leu Ser Arg Ala Gln Thr Val Val Glu Tyr Thr His Asp Ser Asn
             85                  90                  95

Thr Asp Met Phe Gln Ile Gly Arg Ser Thr Glu Ser Pro Ile Asp Phe
            100                 105                 110

Val Val Thr Asp Thr Val Pro Gly Ser Gln Ser Asn Ser Asp Thr Gln
            115                 120                 125

Ser Val Gln Ser Thr Ile Ser Arg Phe Ala Cys Arg Ile Ile Cys Glu
130                 135                 140

Arg Asn Pro Pro Phe Thr Ala Arg Ile Tyr Ala Ala Gly Phe Asp Ser
145                 150                 155                 160

Ser Lys Asn Ile Phe Leu Gly Glu Lys Ala Ala Lys Trp Lys Thr Ser
                165                 170                 175

Asp Gly Gln Met Asp Gly Leu Thr Thr Asn Gly Val Leu Val Met His
            180                 185                 190

Pro Arg Asn Gly Phe Thr Glu Asp Ser Lys Pro Gly Ile Trp Arg Glu
            195                 200                 205

Ile Ser Val Cys Gly Asn Val Phe Ser Leu Arg Glu Thr Arg Ser Ala
            210                 215                 220

Gln Gln Arg Gly Lys Met Val Glu Ile Glu Thr Asn Gln Leu Gln Asp
225                 230                 235                 240

Gly Ser Leu Ile Asp Leu Cys Gly Ala Thr Leu Leu Trp Arg Thr Ala
                245                 250                 255

Glu Gly Leu Ser His Thr Pro Thr Val Lys His Leu Glu Ala Leu Arg
            260                 265                 270

Gln Glu Ile Asn Ala Ala Arg Pro Gln Cys Pro Val Gly Phe Asn Thr
            275                 280                 285

Leu Ala Phe Pro Ser Met Lys Arg Lys Asp Val Val Asp Glu Lys Gln
290                 295                 300

Pro Trp Val Tyr Leu Asn Cys Gly His Val His Gly Tyr His Asn Trp
305                 310                 315                 320

Gly Asn Lys Glu Glu Arg Asp Gly Lys Asp Arg Glu Cys Pro Met Cys
                325                 330                 335

Arg Ser Val Gly Pro Tyr Val Pro Leu Trp Leu Gly Cys Glu Ala Gly
            340                 345                 350

Phe Tyr Val Asp Ala Gly Pro Pro Thr His Ala Phe Ser Pro Cys Gly
            355                 360                 365

His Val Cys Ser Glu Lys Thr Thr Ala Tyr Trp Ser Gln Ile Pro Leu
            370                 375                 380

Pro His Gly Thr His Thr Phe His Ala Ala Cys Pro Phe Cys Ala His
385                 390                 395                 400

Gln Leu Ala Gly Glu Gln Gly Tyr Ile Arg Leu Ile Phe Gln Gly Pro
                405                 410                 415

Leu Asp

<210> SEQ ID NO 3
```

```
<211> LENGTH: 5921
<212> TYPE: DNA
<213> ORGANISM: Homo sapiens
<220> FEATURE:
<221> NAME/KEY: CDS
<222> LOCATION: (501)..(1763)
<223> OTHER INFORMATION: human pellino 2

<400> SEQUENCE: 3
```

| | | |
|---|---|---|
| tccgccgggc cgagggggc ggggagtggg cgcggacggc cccacgcgcc ggggagggg | 60 |
| gcgccccgcg ggccggggg cgggcgcctg gctctgcgtg gggcggggcg gctcccacct | 120 |
| gcccgcgcgc tggccccgc ctccccgcg cggcccagc ctctcgtgcg cccgctccct | 180 |
| cctccttccc tccctcccgc ggggcttcgg cggcggcgct cagcgcaggc aggtcccct | 240 |
| gctgccgggt cccatttgtt gccggctctg actcggggcg gccgcggcgc gcggagctcc | 300 |
| ggggagtcag gcggagcagc gcgcagcca cgacggagca gcagcgggac tggccgcccc | 360 |
| gcgccccctt cgccgccgtg cccttccccg gcgcgctcac cccgttctcg ggatgggatt | 420 |
| gtagcggcgg cgcggactcg gcggggatcg cggcggaggc ggcggcgtcg gcggcggcgt | 480 |

| cgg cgg cca gcg ggg ctc c atg ttt tcc cct ggc cag gag gaa cac tgc gcc | | 533 |
|---|---|---|
| | Met Phe Ser Pro Gly Gln Glu Glu His Cys Ala | |
| | 1 5 10 | |

| ccc aat aag gag cca gtg aaa tac ggg gag ctg gtg gtg ctc ggg tac | 581 |
|---|---|
| Pro Asn Lys Glu Pro Val Lys Tyr Gly Glu Leu Val Val Leu Gly Tyr | |
| 15 20 25 | |

| aat ggt gct tta ccc aat gga gat aga gga cgg agg aaa agt aga ttt | 629 |
|---|---|
| Asn Gly Ala Leu Pro Asn Gly Asp Arg Gly Arg Arg Lys Ser Arg Phe | |
| 30 35 40 | |

| gcc ctc tac aag cgg ccc aag gca aat ggt gtc aaa ccc agc acc gtc | 677 |
|---|---|
| Ala Leu Tyr Lys Arg Pro Lys Ala Asn Gly Val Lys Pro Ser Thr Val | |
| 45 50 55 | |

| cat gtg ata tcc acg ccc cag gca tcc aag gct atc agc tgc aaa ggt | 725 |
|---|---|
| His Val Ile Ser Thr Pro Gln Ala Ser Lys Ala Ile Ser Cys Lys Gly | |
| 60 65 70 75 | |

| caa cac agt ata tcc tac act ttg tca agg aat cag act gtg gtg gtg | 773 |
|---|---|
| Gln His Ser Ile Ser Tyr Thr Leu Ser Arg Asn Gln Thr Val Val Val | |
| 80 85 90 | |

| gag tac aca cat gat aag gat acg gat atg ttt cag gtg ggc aga tca | 821 |
|---|---|
| Glu Tyr Thr His Asp Lys Asp Thr Asp Met Phe Gln Val Gly Arg Ser | |
| 95 100 105 | |

| aca gaa agc cct atc gac ttc gtt gtc aca gac acg att tct ggc agc | 869 |
|---|---|
| Thr Glu Ser Pro Ile Asp Phe Val Val Thr Asp Thr Ile Ser Gly Ser | |
| 110 115 120 | |

| cag aac acg gac gaa gcc cag atc aca cag agc acc ata tcc agg ttc | 917 |
|---|---|
| Gln Asn Thr Asp Glu Ala Gln Ile Thr Gln Ser Thr Ile Ser Arg Phe | |
| 125 130 135 | |

| gcc tgc agg atc gtg tgc gac agg aat gaa cct tac aca gca cgg ata | 965 |
|---|---|
| Ala Cys Arg Ile Val Cys Asp Arg Asn Glu Pro Tyr Thr Ala Arg Ile | |
| 140 145 150 155 | |

| ttc gcc gcc gga ttt gac tct tcc aaa aac ata ttt ctt gga gaa aag | 1013 |
|---|---|
| Phe Ala Ala Gly Phe Asp Ser Ser Lys Asn Ile Phe Leu Gly Glu Lys | |
| 160 165 170 | |

| gca gca aag tgg aaa aac ccc gac ggc cac atg gat ggg ctc act act | 1061 |
|---|---|
| Ala Ala Lys Trp Lys Asn Pro Asp Gly His Met Asp Gly Leu Thr Thr | |
| 175 180 185 | |

| aat ggc gtc ctg gtg atg cat cca cga ggg ggc ttc acc gag gag tcc | 1109 |
|---|---|
| Asn Gly Val Leu Val Met His Pro Arg Gly Gly Phe Thr Glu Glu Ser | |
| 190 195 200 | |

| cag ccc ggg gtc tgg cgc gag atc tct gtc tgt gga gat gtg tac acc | 1157 |
|---|---|

```
                                        -continued

Gln Pro Gly Val Trp Arg Glu Ile Ser Val Cys Gly Asp Val Tyr Thr
    205                 210                 215 ttg cga gaa acc agg tcg gcc cag caa cga gga aag ctg gtg gaa agt      1205
Leu Arg Glu Thr Arg Ser Ala Gln Gln Arg Gly Lys Leu Val Glu Ser
220                 225                 230                 235 gag acc aac gtc ctg cag gac ggc tcc ctc att gac ctg tgt ggg gcc      1253
Glu Thr Asn Val Leu Gln Asp Gly Ser Leu Ile Asp Leu Cys Gly Ala
                240                 245                 250 act ctc ctc tgg aga aca gca gat ggg ctt ttt cat act cca act cag      1301
Thr Leu Leu Trp Arg Thr Ala Asp Gly Leu Phe His Thr Pro Thr Gln
            255                 260                 265 aag cac ata gaa gcc ctc cgg cag gag att aac gcc gcc cgg cct cag      1349
Lys His Ile Glu Ala Leu Arg Gln Glu Ile Asn Ala Ala Arg Pro Gln
        270                 275                 280 tgt cct gtg ggg ctc aac acc ctg gcc ttc ccc agc atc aac agg aaa      1397
Cys Pro Val Gly Leu Asn Thr Leu Ala Phe Pro Ser Ile Asn Arg Lys
    285                 290                 295 gag gtg gtg gag gag aag cag ccc tgg gca tat ctc agt tgt ggc cac      1445
Glu Val Val Glu Glu Lys Gln Pro Trp Ala Tyr Leu Ser Cys Gly His
300                 305                 310                 315 gtg cac ggg tac cac aac tgg ggc cat cgg agt gac acg gag gcc aac      1493
Val His Gly Tyr His Asn Trp Gly His Arg Ser Asp Thr Glu Ala Asn
                320                 325                 330 gag agg gag tgt ccc atg tgc agg act gtg ggc ccc tat gtg cct ctc      1541
Glu Arg Glu Cys Pro Met Cys Arg Thr Val Gly Pro Tyr Val Pro Leu
            335                 340                 345 tgg ctt ggc tgt gag gca gga ttt tat gta gac gca gga ccg cca act      1589
Trp Leu Gly Cys Glu Ala Gly Phe Tyr Val Asp Ala Gly Pro Pro Thr
        350                 355                 360 cat gct ttc act ccc tgt gga cac gtg tgc tcg gag aag tct gca aaa      1637
His Ala Phe Thr Pro Cys Gly His Val Cys Ser Glu Lys Ser Ala Lys
    365                 370                 375 tac tgg tct cag atc ccg ttg cct cat gga act cat gca ttt cac gct      1685
Tyr Trp Ser Gln Ile Pro Leu Pro His Gly Thr His Ala Phe His Ala
380                 385                 390                 395 gct tgc cct ttc tgt gct aca cag ctg gtt ggg gag caa aac tgc atc      1733
Ala Cys Pro Phe Cys Ala Thr Gln Leu Val Gly Glu Gln Asn Cys Ile
                400                 405                 410 aaa tta att ttc caa ggt cca att gac tga cgcccttgac agccatctac        1783
Lys Leu Ile Phe Gln Gly Pro Ile Asp
            415                 420 gactttatta acaggttact gtgaagattt tgccactaac tctagatttt acctttttgt    1843
aatgctgttt atcagaggag ggtgacaggg gctggaaata aagagagggg acatggtgat    1903
gaaacatggc aggagtgtaa cagataccag tggtgtgttg catgctcaaa acagcagcgt    1963
cgtcattgaa gtctgcttga ttaaaccata atatctttgt aataattgga tttaaaatgc    2023
tatgcttcta ttttaaccct tgggttttta accaagtttt ttttttttt tgtaatcttg     2083 gacaagactt taaatcatat tttacagatg tagaagaaat ttattcaaaa gtgtgggctc    2143
atgaagttca cttcagtgca gtgtggtgta ggtgttacgc gaagggcgca cagtgtctag    2203
aaatacttga tcgtggctca aacctgacca gacagcagag gggcggctct gtacagtgtg    2263
actggtggac agatgccctt aggcacaggt ggttttgaaa tctggggctt tttctgattt    2323 attttttctga cttgttgggg gagagaatat tcataacttg tgggcttttt ttttttttaa   2383
cttcagtgga atttactttta gatattcatt catcaaatac atgggacttc acaaacaatt   2443
ttccataact ttttagcctg tcttttgtta tttctgccta atatgatttg ccccgatact    2503
```

-continued

```
catcttgcac ggccagaact gtttggttga ttaaaataca tcagctctta aaaactcatt        2563
aactgagggt aattacagta gtagacatgg tctgggtact atactaccat gtttatttgc        2623
tgactgaatt aagatttaag aatgattaaa aataagcttt tactttttaa aaccacttga        2683
ggtttcataa agcttggggt ttttttttt cctttgttaa gaaagccaac caatcacaat         2743
gatatagtca ttgttgtgca ctccctttc accatctgtc accttcccctt gcagcttaag        2803 gagcccagta agttttgaaa atgtttgcga atcaaactaa atttaagtgg gatgattaga        2863
tatacacaac accaagtggt acatctgcag agataattca aaattcctgc ttttgagaga        2923
gcaaatgagt gtttgctgag gaataattaa atgagaattt cataggagct ccaccattcc        2983
tgttactttc atttcatttt gattaataat tcttggatgc ttggcatcga tcgtatcact        3043
gctcctagaa ggtaaagatc ctttaggaca tgagactggt agaagctggc tgagataaaa        3103
taagtattta tttaaactaa tgttctctta atttgaccat tgcagatttg ggtgactttt        3163
ttttaacctt tgtacatata cgtaatttat atgattctaa tgtactatat ccatacttga        3223
attggttttt tcgtattttg cctactggca atatttgc ctattttcag tcgttctaac          3283
ctatttgaat acgcttttcc ttaaagtgat acgataatat tactcttgat tgctgctgct        3343
taatttgatg taatatgttt aaagttcagc ctctcagttt taatatagct ttattttca         3403 gtggagatca ttgttagga tgagacattt ttggttttgg ttttgtttgg gtaaatttta        3463
aatggtgtga aaatcgatga caacagtcct cttacagata gcttgctgta ttctgtatag        3523
cttactctac ctgcagacag aaaatgaaag aaaaaaatgg acttgcctag aataatatat        3583
tgaatgcctt ttgatttagc cagagtctct gatgattagc tttcgctgat agagtatgtc        3643
ttttcagcct gtaattcttt gggccccaaa gaatgacaaa ggaggcactc gttctcttt         3703 cttgctgtat gcctagaaag tggttgaagg attcttgatg ccctaaaacc atcttgtaag        3763
ctaaatggtc ttgcatccag aaaggccaga ttttacctac caagaaaaaa agatatttt         3823 ccagagagtt aggtatatca taattttcca tttcaagtcc tgtttataag tctagtcatt        3883
ctgcaacgtg acatatcccc caaaatgaag ttaccttcca agttggacac gtcccgtagt        3943
tgggcatatg tctaactaaa agtttctgac ttttagtaaa ttcagcttaa atataagttg        4003
aaatttggga ataatttcc aagctcttgg aagggtaac agtgaaccgc cctccatggg          4063
ctccacatct tttcctttgg cttccaaagt caggtcccgc ccaccctgcc taaggaactg        4123
cagagaggtg gcaaatcagc aaaaaggaca ccaggctctt cttggccact tgtaggaaga        4183 tcccttttaca attttgacta aggagatttt tttttcaca gttgagttag tttgtgaaaa        4243
taaagaactc tgtagctcac caaggtggag aaacgcaatt cagaaaagta atttctccaa        4303
ggtcacttct ttttttatgt cttgccatca ctttaaagga ctagccccac tccccatgt         4363 gtatacacaa ggaaattgca gaccaattag ttgtcttggc ctgactctaa tgccttttgc        4423
aagtagcttt ccagaagtaa aagtcccagt gatgtattcc catagaaata ttttttcagtt       4483 gtttatgtcg tttactacaa aaaaaagat tcagagtgga tggagtacaa ctctgagtat        4543
ttttctagtc cggaattttt tattaataat cggtgctgcc gggtcatgca tgctgcaact        4603
ctcaacattt cccttatttg gttcagcttt tagcaaaaag ggctacagtt caccctgcag        4663
agtattaagg tttctggatt ttttttctccc aactgtggcc caaagaatt aaaatctgtt        4723 aatataaata gagaacatat ttatcattcc tcgatagtta attatagact ttggtacctt        4783
tgtgcctcag ggaagccacg tgatataact ggttatagaa tttcagggtt aggtttaaa        4843 gaaaggagaa agccattgga aaaatgatgg gctccattaa ggagactaat gaatctggat        4903
```

```
gcagaaatat gtcagaaact ggcataaaca tgattgtagt agaatttatt ttccagtacc    4963
aatagggaaa ttattttaag ttattacatt tactgtattg ggaaacttga ggagaactct    5023
ttagttcata aagcttcaat gtctttttt tttttttca tggaaaaact caaacctctg      5083
ttatttggga gctcagtatt gtgtggacac ttacgagagt tttctgctta attgaagtgt    5143
aatataggtt gtagaattgt tacctgcagt tctatggttt tgtttcactt cttttcttt    5203 ttaaagccat tctgttcttt ggatgtgctt gaaagggtgt gtgattacac cattgttaat   5263
gctgggtaaa aactatcttc ttgcagcctt gcctcataac agtggaattt ctgatagaca   5323
aaccacagga ctttgatttt aagccaaatc catctccatc cctttactgt caatcttctg   5383
tcccagtagt ttagcctttg tggcttaggt tatgatgcgc ctccttctgt gcgaccaatg   5443
agacgacttc agcatctttt taaaataatc taagcatcat tgaagcagta acacaaaaaa   5503
aaggttcagt attttctttt tagtataact tacatccttt caaataagtc tttgccctca   5563
tgaagaatcc ctagaggaag ataaggaaaa taagtatttt ccagttttgc ttgacagttt   5623
ctaaacaaac aaaataaac tcaatgaaag gaaagatgtt tcttttagc tgagatgaca    5683 gattgcttct ctgtattaaa tagtctagaa gttaagggga tggtcacatt taccatgtat   5743
tgtgttatta gcagttaaat tttatgaata tgtttgtaaa attgttgttt tatatttcat   5803
gtcaaattga aaagtttatt tcttcactat tgtacctgtg gaaatacaag ccatttaca    5863 ggaaaaaatc ttcaaaaact attaaatgga tatcagcctg aaaaaaaaaa aaaaaaag    5921
```

<210> SEQ ID NO 4
<211> LENGTH: 420
<212> TYPE: PRT
<213> ORGANISM: Homo sapiens
<220> FEATURE:
<223> OTHER INFORMATION: human pellino 2

<400> SEQUENCE: 4

```
Met Phe Ser Pro Gly Gln Glu Glu His Cys Ala Pro Asn Lys Glu Pro
1               5                   10                  15

Val Lys Tyr Gly Glu Leu Val Val Leu Gly Tyr Asn Gly Ala Leu Pro
            20                  25                  30

Asn Gly Asp Arg Gly Arg Arg Lys Ser Arg Phe Ala Leu Tyr Lys Arg
        35                  40                  45

Pro Lys Ala Asn Gly Val Lys Pro Ser Thr Val His Val Ile Ser Thr
    50                  55                  60

Pro Gln Ala Ser Lys Ala Ile Ser Cys Lys Gly Gln His Ser Ile Ser
65                  70                  75                  80

Tyr Thr Leu Ser Arg Asn Gln Thr Val Val Glu Tyr Thr His Asp
                85                  90                  95

Lys Asp Thr Asp Met Phe Gln Val Gly Arg Ser Thr Glu Ser Pro Ile
            100                 105                 110

Asp Phe Val Val Thr Asp Thr Ile Ser Gly Ser Gln Asn Thr Asp Glu
        115                 120                 125

Ala Gln Ile Thr Gln Ser Thr Ile Ser Arg Phe Ala Cys Arg Ile Val
    130                 135                 140

Cys Asp Arg Asn Glu Pro Tyr Thr Ala Arg Ile Phe Ala Ala Gly Phe
145                 150                 155                 160

Asp Ser Ser Lys Asn Ile Phe Leu Gly Glu Lys Ala Ala Lys Trp Lys
                165                 170                 175

Asn Pro Asp Gly His Met Asp Gly Leu Thr Thr Asn Gly Val Leu Val
```

-continued

```
                180             185             190
Met His Pro Arg Gly Gly Phe Thr Glu Glu Ser Gln Pro Gly Val Trp
        195                 200                 205
Arg Glu Ile Ser Val Cys Gly Asp Val Tyr Thr Leu Arg Glu Thr Arg
    210                 215                 220
Ser Ala Gln Gln Arg Gly Lys Leu Val Glu Ser Glu Thr Asn Val Leu
225                 230                 235                 240
Gln Asp Gly Ser Leu Ile Asp Leu Cys Gly Ala Thr Leu Leu Trp Arg
                245                 250                 255
Thr Ala Asp Gly Leu Phe His Thr Pro Thr Gln Lys His Ile Glu Ala
            260                 265                 270
Leu Arg Gln Glu Ile Asn Ala Ala Arg Pro Gln Cys Pro Val Gly Leu
        275                 280                 285
Asn Thr Leu Ala Phe Pro Ser Ile Asn Arg Lys Glu Val Val Glu Glu
    290                 295                 300
Lys Gln Pro Trp Ala Tyr Leu Ser Cys Gly His Val His Gly Tyr His
305                 310                 315                 320
Asn Trp Gly His Arg Ser Asp Thr Glu Ala Asn Glu Arg Glu Cys Pro
                325                 330                 335
Met Cys Arg Thr Val Gly Pro Tyr Val Pro Leu Trp Leu Gly Cys Glu
            340                 345                 350
Ala Gly Phe Tyr Val Asp Ala Gly Pro Pro Thr His Ala Phe Thr Pro
        355                 360                 365
Cys Gly His Val Cys Ser Glu Lys Ser Ala Lys Tyr Trp Ser Gln Ile
    370                 375                 380
Pro Leu Pro His Gly Thr His Ala Phe His Ala Ala Cys Pro Phe Cys
385                 390                 395                 400
Ala Thr Gln Leu Val Gly Glu Gln Asn Cys Ile Lys Leu Ile Phe Gln
                405                 410                 415
Gly Pro Ile Asp
            420

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer PELD1

<400> SEQUENCE: 5
atgttttccc ctggccagga ggaacac                                        27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer PELD2

<400> SEQUENCE: 6
tcagtcaatt ggaccttgga aaattaa                                        27

<210> SEQ ID NO 7
<211> LENGTH: 22
<212> TYPE: DNA
<213> ORGANISM: Artificial Sequence
<220> FEATURE:
```

```
<223> OTHER INFORMATION: Description of Artificial Sequence:
      oligonucleotide probe N63226QF to pellino 2 3' untranslated region

<400> SEQUENCE: 7
gatgctgaag tcgtctcatt gg                                              22

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:
      oligonucleotide probe N63226QR to pellino 2 3' untranslated region

<400> SEQUENCE: 8
ccagtagttt agcctttgtg gctt                                            24

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
      oligonucleotide probe N63226QP to pellino 2 3' untranslated region
<220> FEATURE:
<221> NAME/KEY: modified_base
<222> LOCATION: (1)
<223> OTHER INFORMATION: n = c modified by 6-FAM
<220> FEATURE:
<221> NAME/KEY: modified_base
<222> LOCATION: (25)
<223> OTHER INFORMATION: n = c modified by TAMRA

<400> SEQUENCE: 9
ngcacagaag gaggcgcatc ataan                                           25

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:reference
      probe TLF7QF representing single copy region in human
      genome

<400> SEQUENCE: 10
ggtctctatt tgcacttggc tgat                                            24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:reference
      probe TLF7QR representing single copy region in human
      genome

<400> SEQUENCE: 11
ttttcattgt tgaccaagct agaca                                           25

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:reference
      probe TLF7QP representing single copy region in human
      genome
<220> FEATURE:
```

-continued

```
<221> NAME/KEY: modified_base
<222> LOCATION: (1)
<223> OTHER INFORMATION: n = t modified by 6-FAM
<220> FEATURE:
<221> NAME/KEY: modified_base
<222> LOCATION: (29)
<223> OTHER INFORMATION: n = t modified by TAMRA

<400> SEQUENCE: 12
nagggcatac tgcctgcata tttcctgcn                                    29

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 13

Met Phe Ser Pro
  1

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 14

Pro Val Lys Tyr Gly Glu Leu
  1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 15

Val Leu Gly Tyr Asn Gly
  1               5

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 16

Leu Pro Asn Gly Asp Arg Gly Arg Arg Lys Ser Arg Phe Ala Leu
  1               5                  10                  15

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence:amino acid
```

```
    sequence identity in comparison of pellino 1 and
    pellino 2

<400> SEQUENCE: 17

Lys Arg Pro Lys Ala Asn Gly Val Lys Pro Ser Thr Val His
  1               5                  10

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:amino acid
    sequence identity in comparison of pellino 1 and
    pellino 2

<400> SEQUENCE: 18

Thr Pro Gln Ala
  1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:amino acid
    sequence identity in comparison of pellino 1 and
    pellino 2

<400> SEQUENCE: 19

Lys Ala Ile Ser
  1

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence:amino acid
    sequence identity in comparison of pellino 1 and
    pellino 2

<400> SEQUENCE: 20

Gln His Ser Ile Ser Tyr Thr Leu Ser Arg
  1               5                  10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence:amino acid
    sequence identity in comparison of pellino 1 and
    pellino 2

<400> SEQUENCE: 21

Gln Thr Val Val Val Glu Tyr Thr His Asp
  1               5                  10

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:amino acid
    sequence identity in comparison of pellino 1 and
    pellino 2

<400> SEQUENCE: 22
```

```
Thr Asp Met Phe Gln
  1               5

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 23

Gly Arg Ser Thr Glu Ser Pro Ile Asp Phe Val Val Thr Asp Thr
  1               5                  10                  15

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 24

Gln Ser Thr Ile Ser Arg Phe Ala Cys Arg Ile
  1               5                  10

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 25

Thr Ala Arg Ile
  1

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 26

Ala Ala Gly Phe Asp Ser Ser Lys Asn Ile Phe Leu Gly Glu Lys Ala
  1               5                  10                  15

Ala Lys Trp Lys
             20

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 27
```

```
Met Asp Gly Leu Thr Thr Asn Gly Val Leu Val Met His Pro Arg
1               5                   10                  15
```

```
<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 28

Gly Phe Thr Glu
1
```

```
<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 29

Trp Arg Glu Ile Ser Val Cys Gly
1               5
```

```
<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 30

Leu Arg Glu Thr Arg Ser Ala Gln Gln Arg Gly Lys
1               5                   10
```

```
<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 31

Leu Gln Asp Gly Ser Leu Ile Asp Leu Cys Gly Ala Thr Leu Leu Trp
1               5                   10                  15

Arg Thr Ala
```

```
<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 32

His Thr Pro Thr
1
```

```
<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 33

Glu Ala Leu Arg Gln Glu Ile Asn Ala Ala Arg Pro Gln Cys Pro Val
 1               5                  10                  15

Gly

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 34

Asn Thr Leu Ala Phe Pro Ser
 1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 35

Glu Lys Gln Pro Trp
 1               5

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 36

Cys Gly His Val His Gly Tyr His Asn Trp Gly
 1               5                  10

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 37

Arg Glu Cys Pro Met Cys Arg
 1               5
```

```
<210> SEQ ID NO 38
<211> LENGTH: 26
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 38

Val Gly Pro Tyr Val Pro Leu Trp Leu Gly Cys Glu Ala Gly Phe Tyr
  1               5                  10                  15

Val Asp Ala Gly Pro Pro Thr His Ala Phe
             20                  25

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 39

Pro Cys Gly His Val Cys Ser Glu Lys
  1               5

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 40

Tyr Trp Ser Gln Ile Pro Leu Pro His Gly Thr His
  1               5                  10

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 41

Phe His Ala Ala Cys Pro Phe Cys Ala
  1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence:amino acid
      sequence identity in comparison of pellino 1 and
      pellino 2

<400> SEQUENCE: 42

Leu Ile Phe Gln Gly Pro
  1               5
```